United States Patent
Daidoji et al.

(10) Patent No.: US 10,617,287 B2
(45) Date of Patent: Apr. 14, 2020

(54) ENDOSCOPE SYSTEM AND ENDOSCOPE LIGHT SOURCE APPARATUS

(71) Applicant: OLYMPUS CORPORATION, Tokyo (JP)

(72) Inventors: Bakusui Daidoji, Hachioji (JP); Takeshi Ito, Hino (JP); Hiroyuki Kamee, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 425 days.

(21) Appl. No.: 15/397,835

(22) Filed: Jan. 4, 2017

(65) Prior Publication Data

US 2017/0112370 A1 Apr. 27, 2017

Related U.S. Application Data

(63) Continuation of application No. PCT/JP2015/066217, filed on Jun. 4, 2015.

(30) Foreign Application Priority Data

Jul. 9, 2014 (JP) .................................. 2014-141761

(51) Int. Cl.
  *A61B 1/06* (2006.01)
  *A61B 1/04* (2006.01)
  (Continued)

(52) U.S. Cl.
  CPC .......... *A61B 1/0661* (2013.01); *A61B 1/0002* (2013.01); *A61B 1/00009* (2013.01);
  (Continued)

(58) Field of Classification Search
  CPC . A61B 1/0661; A61B 1/00009; A61B 1/0002; A61B 1/04; A61B 1/06;
  (Continued)

(56) References Cited

U.S. PATENT DOCUMENTS

2008/0310181 A1* 12/2008 Gurevich ............. G02B 6/0006
  362/554
2010/0259656 A1* 10/2010 Irion .................. A61B 1/00186
  348/273
(Continued)

FOREIGN PATENT DOCUMENTS

CN    103703310 A    4/2014
JP    S59-069052 A    4/1984
(Continued)

OTHER PUBLICATIONS

English translation of International Preliminary Report on Patentability dated Jan. 19, 2017 together with the Written Opinion received in related International Application No. PCT/JP2015/066217.
(Continued)

Primary Examiner — Timothy J Neal
Assistant Examiner — William B Chou
(74) Attorney, Agent, or Firm — Scully, Scott, Murphy & Presser, P.C.

(57) ABSTRACT

An endoscope system includes an illumination section, a color component ratio measurement section and a light quantity ratio adjustment circuit. The illumination section including a light source sequentially or simultaneously radiates an illumination light being a plurality of narrow-band lights having wavelengths different from each other and having light quantities which are independently controllable each other, on an observation object. The color component ratio measurement section measures a color component ratio of the illumination light. The light quantity ratio adjustment circuit adjusts a light quantity ratio of the narrow-band lights based on an output from the color component ratio measurement section and performs color correction to cause the illumination light to be a desired color.

22 Claims, 15 Drawing Sheets

(51) Int. Cl.
*A61B 1/07* (2006.01)
*G02B 23/24* (2006.01)
*A61B 1/00* (2006.01)

(52) U.S. Cl.
CPC .................. *A61B 1/04* (2013.01); *A61B 1/06* (2013.01); *A61B 1/0638* (2013.01); *A61B 1/07* (2013.01); *G02B 23/2461* (2013.01); *G02B 23/2484* (2013.01)

(58) Field of Classification Search
CPC .... A61B 1/0638; A61B 1/07; G02B 23/2461; G02B 23/2484
See application file for complete search history.

(56) References Cited

U.S. PATENT DOCUMENTS

2012/0176769 A1* 7/2012 Reimer ................ A61B 3/0008 362/84

2014/0140059 A1 5/2014 Tamura et al.

FOREIGN PATENT DOCUMENTS

| JP | S61-099484 A | 5/1986 |
| JP | 2008-158030 A | 7/2008 |
| JP | 2008-284030 A | 11/2008 |
| JP | 2010-158413 A | 7/2010 |

OTHER PUBLICATIONS

Chinese Office Action dated Aug. 28, 2017 in Chinese Patent Application No. 201580036945.1.
International Search Report dated Sep. 8, 2015 issued in PCT/JP2015/066217.
Japanese Office Action dated Sep. 26, 2017 in Japanese Patent Application No. 2016-532500.

* cited by examiner

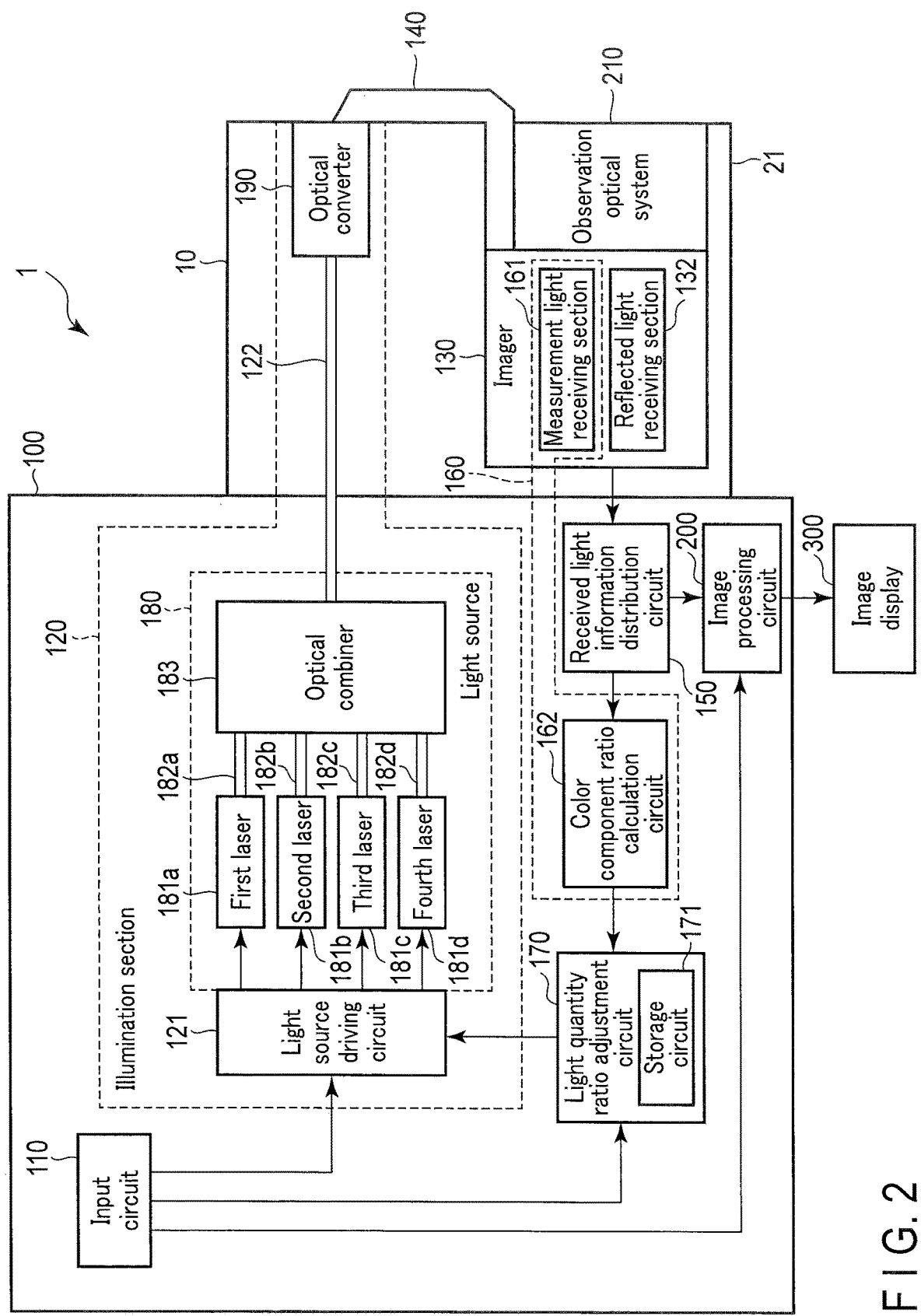
F I G. 2

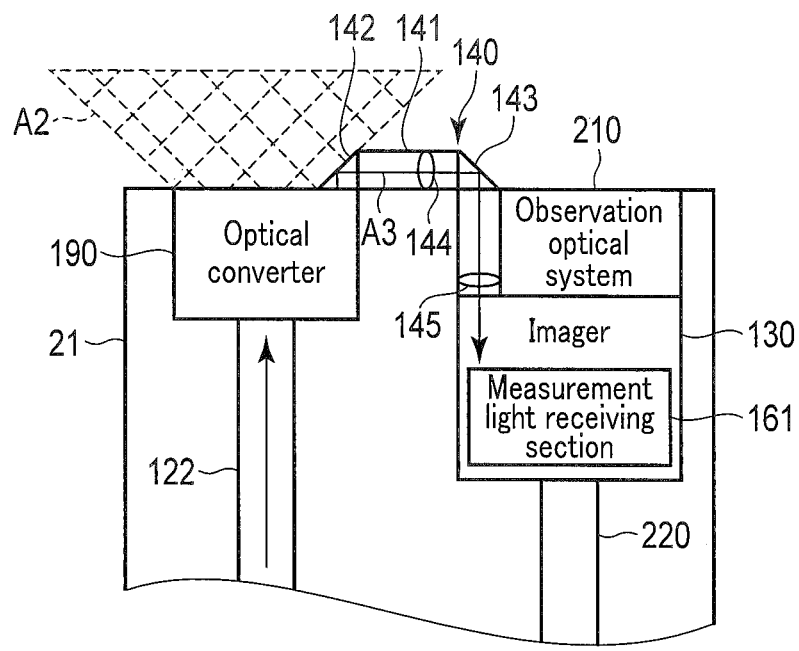
F I G. 6
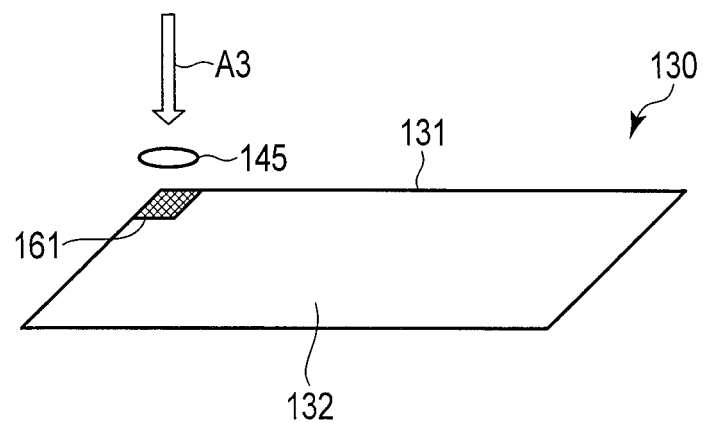
F I G. 7

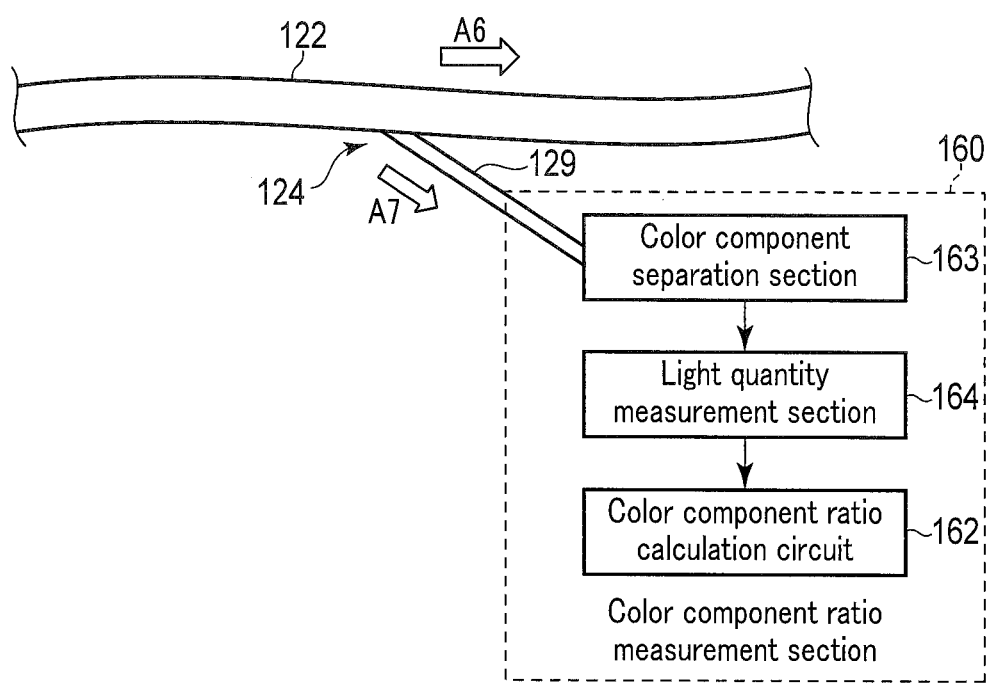
F I G. 16

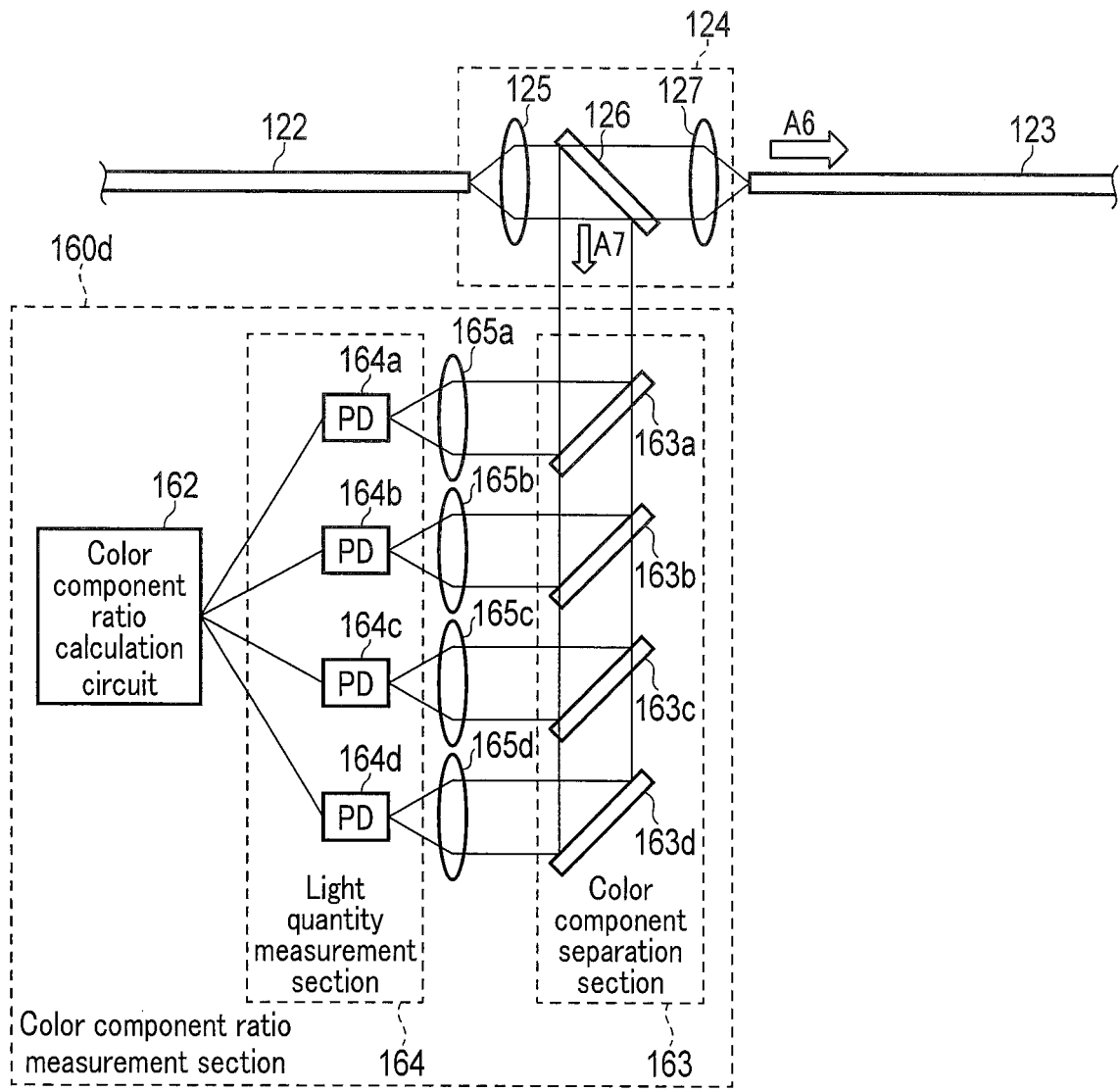
F I G. 17

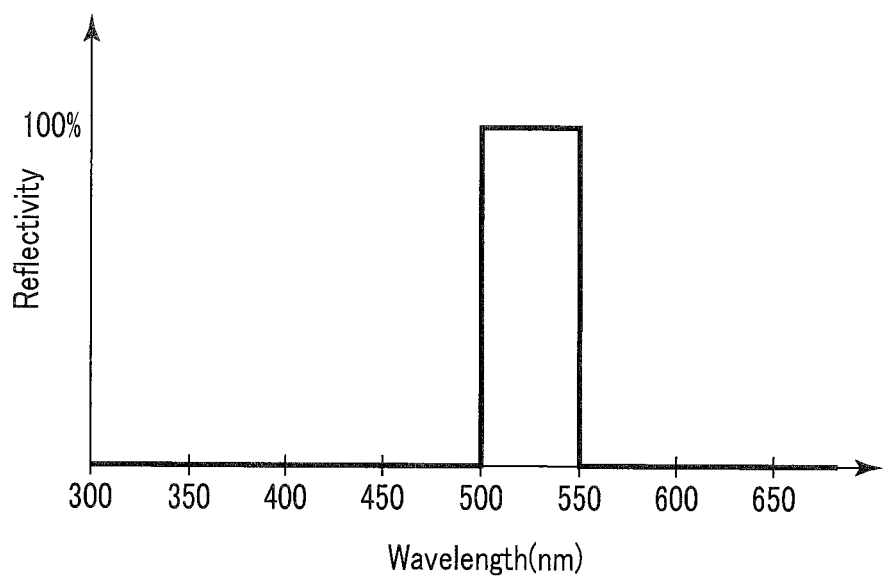
F I G. 20
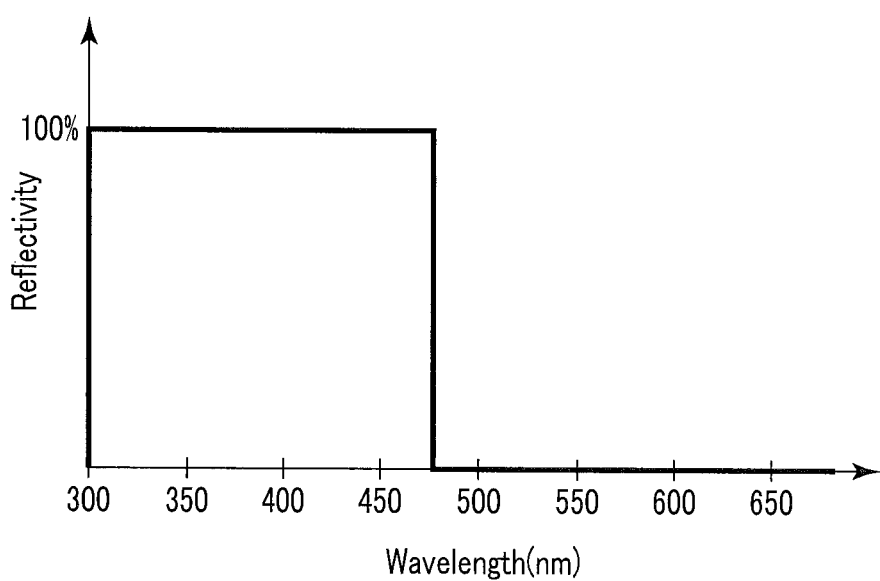
F I G. 21

ENDOSCOPE SYSTEM AND ENDOSCOPE LIGHT SOURCE APPARATUS

CROSS-REFERENCE TO RELATED APPLICATIONS

This application is a Continuation Application of PCT Application No. PCT/JP2015/066217, filed Jun. 4, 2015 and based upon and claiming the benefit of priority from prior the Japanese Patent Application No. 2014-141761, filed Jul. 9, 2014, the entire contents of all of which are incorporated herein by references.

BACKGROUND OF THE INVENTION

1. Field of the Invention

The present invention relates to an endoscope system, which radiates illumination light with which a plurality of narrow-band lights having wavelengths different from each other are mixed on an observation object, to observe the observation object and also relates to a light source apparatus for an endoscope.

2. Description of the Related Art

There is a known endoscope system that observes an observation object by emitting a mixed light of a plurality of laser lights as an illumination light from a distal end of an insertion section. For example, Jpn. Pat. Appln. KOKAI Publication No. 2008-158030 discloses an endoscope system including an illumination apparatus that can generate a uniform illumination light using laser light sources. In the illumination apparatus, a mixed light of a red laser light, a green laser light, and a blue laser light emitted from a light source is used as an illumination light.

BRIEF SUMMARY OF THE INVENTION

According to one embodiment of the present invention, an endoscope system comprises an illumination section, including a light source, which sequentially or simultaneously radiates an illumination light being a plurality of narrow-band lights having wavelengths different from each other and having light quantities which are independently controllable each other, on an observation object. The endoscope system comprises a color component ratio measurement section which measures a color component ratio of the illumination light. The endoscope system comprises a light quantity ratio adjustment circuit which adjusts a light quantity ratio of the narrow-band lights based on an output from the color component ratio measurement section and performs color correction to cause the illumination light to be a desired color.

According to another embodiment of the present invention, an endoscope light source apparatus comprises a light source which sequentially or simultaneously emits an illumination light being a plurality of narrow-band lights having wavelengths different from each other and having light quantities which are independently controllable each other. The endoscope light source apparatus comprises a color component ratio measurement section which measures a color component ratio of the illumination light, and a light quantity ratio adjustment circuit which adjusts a light quantity ratio of the narrow-band lights based on an output from the color component ratio measurement section and performs color correction to cause the illumination light to be a desired color.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 2 is a block diagram showing a main configuration of the endoscope system of the first embodiment.

FIG. 6 is a diagram schematically showing an optical path of a measurement light at a distal end of an insertion section in the first embodiment.

FIG. 7 is a diagram schematically showing a measurement light which falls on a light receiving surface of an image sensor.

FIG. 16 is a diagram schematically showing another example of a measurement light branch and a color component ratio measurement section in the second embodiment.

FIG. 17 is a diagram schematically showing another example of a measurement light branch and a color component ratio measurement section in the second embodiment.

FIG. 20 is a diagram showing an example of a relationship between a wavelength and a reflectivity in a third dichroic mirror of the color component separation section.

FIG. 21 is a diagram showing an example of a relationship between a wavelength and a reflectivity in a fourth dichroic mirror of the color component separation section.

DETAILED DESCRIPTION OF THE INVENTION

First Embodiment

Figure 1:
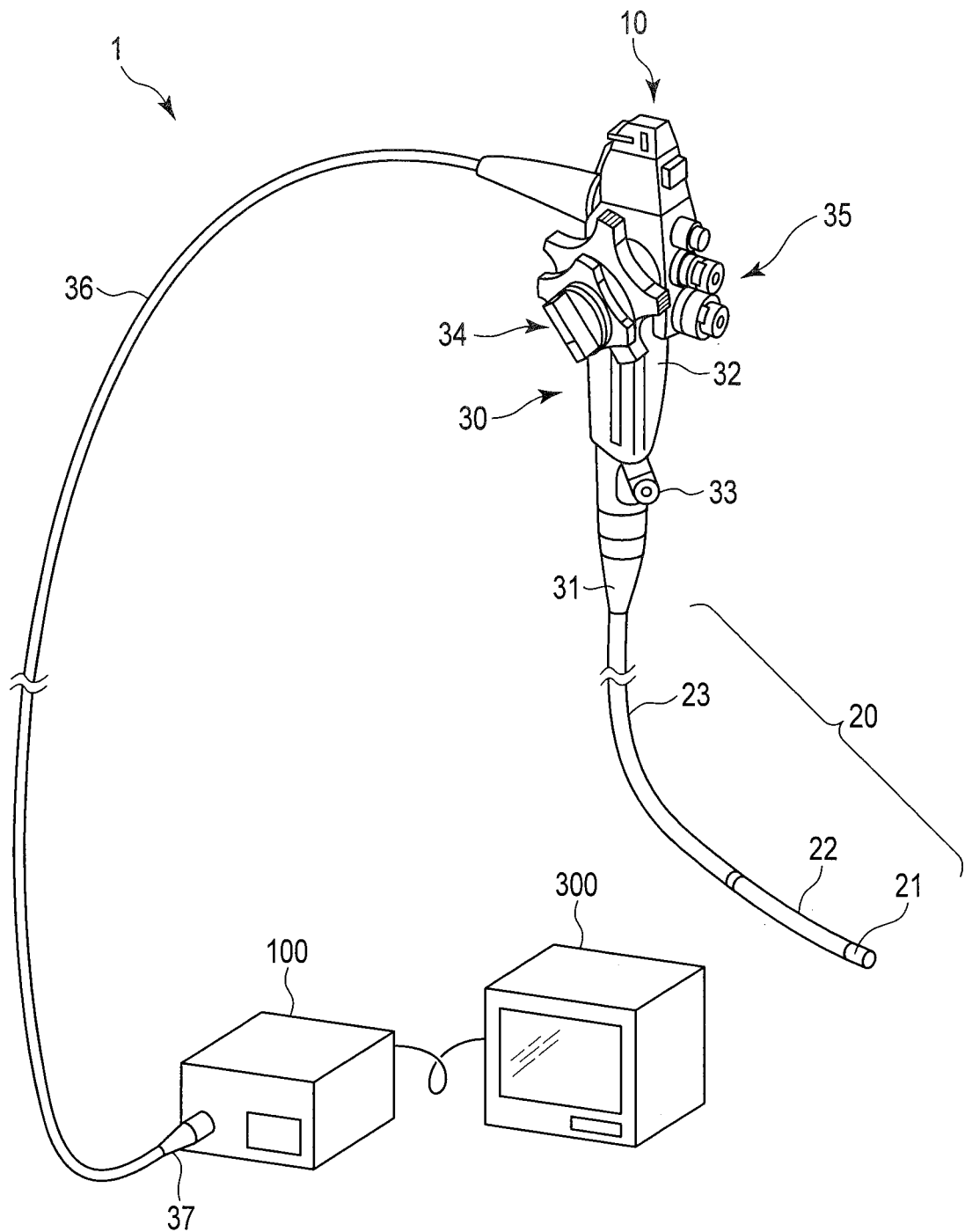
FIG. 1 is a diagram schematically showing an endoscope system of a first embodiment.

FIG. 1 is a diagram schematically showing an endoscope system 1 of the first embodiment of the present invention. The endoscope system 1 comprises an endoscope 10, a main body 100 to be connected to the endoscope 10, and an image display 300 to be connected to the main body 100.

The endoscope 10 comprises a flexible insertion section 20 to be inserted in an insertion target including an observation object, and a control section 30 coupled to a proximal end side of the insertion section 20. The insertion section 20 is an elongate tubular portion at a distal end side of the endoscope and comprises a distal rigid portion 21, a bending portion 22 coupled to a proximal end side of the distal rigid portion 21, and a flexible tube portion 23 coupled to a proximal end side of the bending portion 22. The distal rigid portion 21 incorporates an imager 130, an optical converter 190, an observation optical system 210, etc., which are described later. The bending portion 22 bends in a desired direction by operating the control section 30. The flexible tube portion 23 is freely bendable. For example, it bends along with a bend shape of an insertion target.

The control section 30 comprises a stopper section 31 coupled to a proximal end side of the flexible tube portion 23, and a grip section 32 coupled to a proximal end side of the stopper section 31. The stopper section 31 includes a treatment tool insertion port 33 connected to an insertion channel (not shown) which extends inside the insertion section 20. The grip section 32 includes an operation dial 34 to bend the bending portion 22, and a plurality of switches 35 for air supply, water supply, suction, image capture, etc.

The insertion section 20 and the control section 30 contains an optical fiber 122 having a distal end connected to the optical converter 190 (see FIG. 2) and an imaging cable 220 having a distal end connected to the imager 130 (see FIG. 6) therein, which extend inside the insertion section 20 and the control section 30. The optical fiber 122 and the imaging cable 220 extend sideways from a proximal end side of the grip section 32 and constitute a universal cord 36. A connector 37 is provided at a proximal end of the universal cord 36, and to be detachably connected to the main body 100.

FIG. 2 is a block diagram showing a main configuration of the endoscope system of the first embodiment. The endoscope system 1 comprises an input circuit 110, an illumination section 120, the imager 130, a measurement light guide section 140, a received light information distribution circuit 150, a color component ratio measurement section 160, a light quantity ratio adjustment circuit 170, an image processing circuit 200, and the aforementioned image display 300. The input circuit 110, the received light information distribution circuit 150, the light quantity ratio adjustment circuit 170, and the image processing circuit 200 are arranged in the main body 100. The illumination section 120 and the color component ratio measurement section 160 are arranged ranging from the endoscope 10 to the main body 100. The imager 130 and the measurement light guide section 140 are arranged in the endoscope 10.

(Input Circuit and Observation Mode)

The endoscope system 1 of the present embodiment has two observation modes depending on the purpose of observation; for example, a normal light observation mode and a specific light observation mode. Either one of the two observation modes is input to the input circuit 110 by a user through an input device (not shown) such as a keyboard. Observation mode information input to the input circuit 110 is output to the illumination section 120, the light quantity ratio adjustment circuit 170, and the image processing circuit 200.

The normal light observation mode is an observation mode for reproducing and observing a color of an observation object radiated with a white light, which has high color rendering properties (for example, light emitted from a xenon lamp or a halogen lamp), using a mixed light composed of a plurality of narrow-band lights.

The specific light observation mode is an observation mode for highlighting and observing a specific observation object by radiating light (specific light) having a spectrum different from that of the white light, utilizing characteristics, such as absorption, reflection, and scattering of light, in the specific observation object. In the present embodiment, a mixed light of a violet laser light emitted from a first laser 181a of a light source 180 (to be described later) of the illumination section 120 and a green laser light emitted from a third laser 181c is used as the specific light. The violet laser light has a characteristic of being strongly absorbed by hemoglobin in a capillary vessel near the surface of living tissue. The green laser light has a characteristic of being strongly absorbed by hemoglobin in a thick vessel in a deep part of living tissue. Utilizing these characteristics, when an observation object is radiated with the specific light and predetermined image processing is performed, a capillary vessel and a thick vessel can be observed with enhanced contrast.

The endoscope system 1 has at least the normal light observation mode and the specific light observation mode, and may have any other observation modes. The other observation modes may be a mode for radiating a normal light having a different tone, a mode for performing other specific light observation that highlights an observation object, or a fluorescent observation mode for observing fluorescence that appears when an observation object or a pharmacological agent is radiated with excitation light.

(Illumination Section)

The illumination section 120 comprises the light source 180, a light source driving circuit 121, the optical fiber (illumination light guide section) 122, and the optical converter 190. The light source 180 and the light source driving circuit 121 are arranged in the main body 100. The optical converter 190 is arranged in the distal rigid portion 21 of the insertion section 20. The light source 180 and the optical converter 190 are optically connected through the optical fiber 122.

(Light Source)

The light source 180 comprises the first laser 181a, a second laser 181b, the third laser 181c, and a fourth laser 181d. The lasers 181a to 181d are light sources that generate narrow-band lights having wavelengths different from one another. The first laser 181*a* is a laser that radiates a violet laser light, for example, a laser diode having a center wavelength of 405 nm. The second laser 181*b* is a laser that radiates a blue laser light, for example, a laser diode having a center wavelength of 445 nm. The third laser 181*c* is a laser that radiates a green laser light, for example, a laser diode having a center wavelength of 532 nm. The fourth laser 181*d* is a laser that radiates a red laser light, for example, a laser diode having a center wavelength of 635 nm.

The light source 180 further comprises a first optical fiber 182*a*, a second optical fiber 182*b*, a third optical fiber 182*c*, a fourth optical fiber 182*d*, and an optical combiner 183. The first to fourth optical fibers 182*a* to 182*d* and the optical fiber 122 are single fibers having a core diameter of, for example, several μm to several hundreds μm. Proximal ends of the first to fourth optical fibers 182*a* to 182*d* are optically connected to the first to fourth lasers 181*a* to 181*d*, respectively. Distal ends of the first to fourth optical fibers 182*a* to 182*d* are optically connected to the optical combiner 183. A proximal end of the optical fiber 122 is optically connected to the optical combiner 183.

The first to fourth optical fibers 182*a* to 182*d* guide laser lights respectively emitted from the first to fourth lasers 181*a* to 181*d*. The optical combiner 183 combines the laser lights guided through the first to fourth optical fibers 182*a* to 182*d*. The optical fiber 122 guides the light combined by the optical combiner 183 to the optical converter 190.

An optical coupling lens (not shown) is arranged between each of the lasers 181*a* to 181*d* and the first to fourth optical fibers 182*a* to 182*d* to converge the laser light emitted from each of the lasers 181*a* to 181*d* and couple it to the optical fibers 182*a* to 182*d*.

Narrow-band lights emitted from the lasers 181*a* to 181*d* of the light source 180 may be narrow-band lights of light quantities that are independently controllable each other. LED light sources or the like may be used instead of the laser light sources, and the wavelengths of the lights may be different from those described above. Furthermore, a light source formed by combining a laser light source with a phosphor, which is excited by at least one narrow-band light of a plurality of narrow-band lights, may be used. A narrow-band light means a light having a wavelength spectrum in which the half width is several tens of nm or smaller.

Further, the optical fiber 122 may be replaced with a bundle fiber formed of a bundle of a plurality of optical fibers. If a bundle fiber is used, a lens is arranged in the optical converter 190.

(Light Source Driving Circuit)

The light source driving circuit 121 is connected to the first to fourth lasers 181*a* to 181*d* of the light source 180. The light source driving circuit 121 controls ON/OFF, driving currents, driving systems (continuous wave (CW) driving, pulse driving, high-frequency superposition, etc.) of the first to fourth lasers 181*a*-181*d*.

The light source driving circuit 121 turns on the first to fourth lasers 181*a* to 181*d* based on observation mode information output from the input circuit 110. In the present embodiment, when the normal light observation mode is input to the input circuit 110, the second laser 181*b* (a blue laser light), the third laser 181*c* (a green laser light), and the fourth laser 181*d* (a red laser light) are simultaneously turned on. When the specific light observation mode is input to the input circuit 110, the first laser 181*a* (a violet laser light) and the third laser 181*c* (the green laser light) are simultaneously turned on.

The light quantity ratio of the lasers 181*a* to 181*d* in the normal light observation mode or the specific light observation mode follows input current values input to the respective lasers. The input current values are set in advance so that an illumination light made of the laser lights presents a desired color. In this specification, "a desired color" refers to a color of an illumination light set in advance that allows an observation object to be seen in a color appropriate to the purpose. For example, a desired color in the normal light observation mode refers to a color that reproduces a color of an observation object radiated with a white light, which has high color rendering properties (for example, light emitted from a xenon lamp or a halogen lamp). This is set on the basis of a color rendering index and a color temperature. A desired color in the specific light observation mode refers to a color that allows blood vessels in a surface layer and a deep layer in the observation object to be highlighted. Furthermore, "an illumination light" in this specification refers to a mixed light of a plurality of narrow-band lights that has not been radiated on the observation object or reflected by the observation object.

(Optical Converter)

Figure 3:
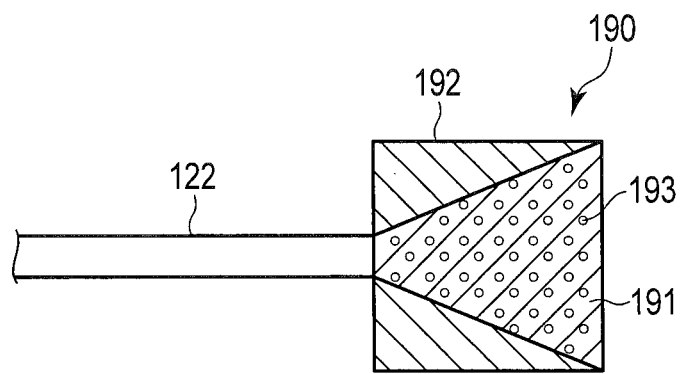
FIG. 3 is a diagram schematically showing an optical converter.

The optical converter 190 is arranged in an illumination window (not shown) at a distal end surface of the distal rigid portion 21 of the insertion section 20. FIG. 3 is a diagram schematically showing the optical converter 190. The optical converter 190 comprises an optical diffuser 191 optically connected to the distal end of the optical fiber 122, and a holder 192 holding the optical diffuser 191. The optical diffuser 191 includes, for example, alumina particles 193. The optical diffuser 191 has a function of diffusing the illumination light guided through the optical fiber 122 to expand light distribution. The optical diffuser 191 may be replaced with a lens, or the optical diffuser 191 may be used in combination with a lens.

(Imager and Color Component Ratio Measurement Section (Measurement Light Receiving Section))

Referring back to FIG. 2, the imager 130 is arranged in the distal rigid portion 21 of the insertion section 20. The imager 130 is optically connected to the observation optical system 210 arranged in the illumination window (not shown) at the distal end surface of the distal rigid portion 21. The imager 130 is also connected to the received light information distribution circuit 150 through the imaging cable 220 (refer to FIG. 6) extending from the endoscope 10 to the main body 100. The imager 130 comprises an image sensor 131, such as a CCD imager or a CMOS imager.

Figure 4A:
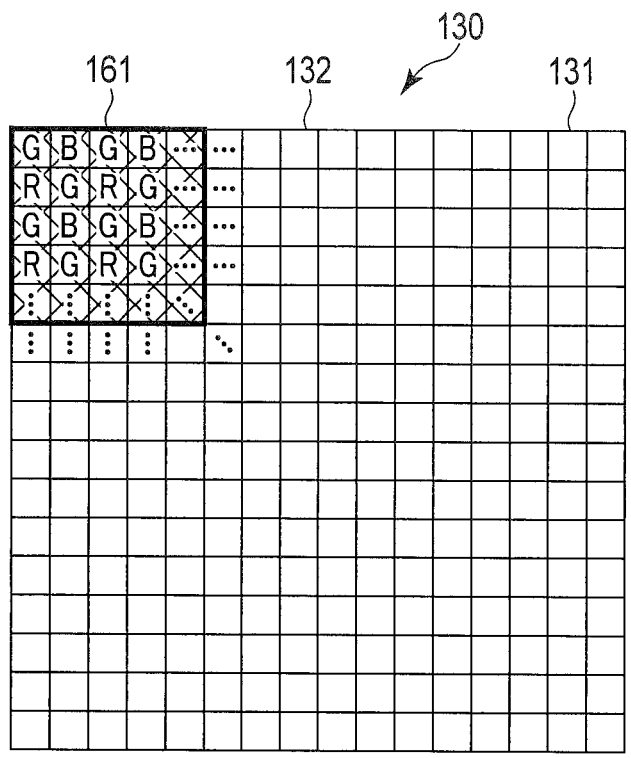
FIG. 4A is a diagram schematically showing a light receiving surface of a color CCD as an image sensor.
Figure 4B:
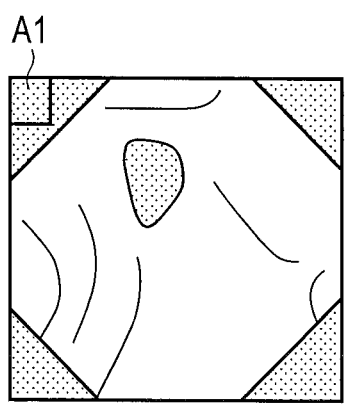
FIG. 4B is a diagram schematically showing an example of an observation object image acquired by the image sensor of FIG. 4A.

FIG. 4A is a diagram schematically showing a light receiving surface of the image sensor 131. FIG. 4B is a diagram schematically showing an observation object image on the light receiving surface which is shown in FIG. 4A and utilized as an observation viewing field. The image sensor 131 shown in FIG. 4A is a color CCD. The light receiving surface of the image sensor 131 includes a reflected light receiving section 132, which is a pixel area for use in generation of an observation object image. The reflected light receiving section 132 receives a reflected light of the illumination light taken in by the observation optical system 210 and reflected by the observation object, and photoelectrically converts the reflected light to an electric signal including reflected light information. In this specification, "reflected light" refers to alight obtained by reflecting an illumination light by the observation object. This is distinct from an illumination light in that a color component ratio differs from that of the illumination light due to light absorption or the like in the observation object.

The light receiving surface of the image sensor 131 includes a measurement light receiving section 161, which is a pixel area different from the pixel area used as the reflected light receiving section 132. The pixel area used as the measurement light receiving section 161 is, for example, a shaded portion at a corner area in the light receiving surface shown in FIG. 4A. The measurement light receiving section 161 is not used for generation of an observation object image. The measurement light receiving section 161 and a color component ratio calculation circuit 162 (to be described later) form the color component ratio measurement section 160 that measures a ratio of color components of the illumination light. The measurement light receiving section 161 is an area exclusive of the reflected light receiving section 132 of the light receiving surface of the image sensor 131. The measurement light receiving section 161 is smaller than the reflected light receiving section 132.

The measurement light receiving section 161 receives part of the illumination light guided by the measurement light guide section 140 as a measurement light, and photoelectrically converts the received light to an electric signal including measurement light information. The measurement light information is, for example, a pixel value in at least three wavelength regions of a red region, a green region, and a blue region of the measurement light. In this specification, "measurement light" refers to a light part branched from the illumination light and used for color component ratio measurement. In other words, the measurement light has the same color component ratio as that of the illumination light and is not radiated on the observation object.

The reflected light information acquired by the reflected light receiving section 132 and the measurement light information acquired by the measurement light receiving section 161 on the light receiving surface of the image sensor 131 are transmitted as electric signals from the image sensor 131 to the received light information distribution circuit 150 through the imaging cable 220.

In the present embodiment, a part of the imager 130, for example, a corner area of the light receiving surface of the image sensor 131 is used as the measurement light receiving section 161. This is because a corner area of the light receiving surface of the image sensor 131 is not used for generation of an observation object image, as represented by an area A1 in FIG. 4B. Thus, in the present embodiment, an additional image sensor or the like need not be used as the measurement light receiving section 161. Instead, an unused pixel area on the light receiving surface of the existing image sensor 131 is used as the measurement light receiving section 161, that is, the area is exclusive of the area contributing to generation of an observation object image on the light receiving surface of the existing image sensor 131 of the imager 130.

The measurement light receiving section 161 comprises at least a set of three color filters of R, G, and B. To measure a color component ratio of a measurement light with satisfactory accuracy, the measurement light receiving section 161 preferably comprises a plurality of sets of color filters as shown in FIG. 4A. A CCD light receiving element has several-μm pitches. Accordingly, the area of the measurement light receiving section 161 is, for example, several $\mu m^2$ to several tens of $\mu m^2$. The size is equal to or smaller than the area not used for generation of an observation object image as described above. Furthermore, the measurement light receiving section 161 is set to an area sufficiently larger than an irradiation area of the measurement light guided by the measurement light guide section 140, so that the measurement light may not fall on the reflected light receiving section 132.

Figure 5A:
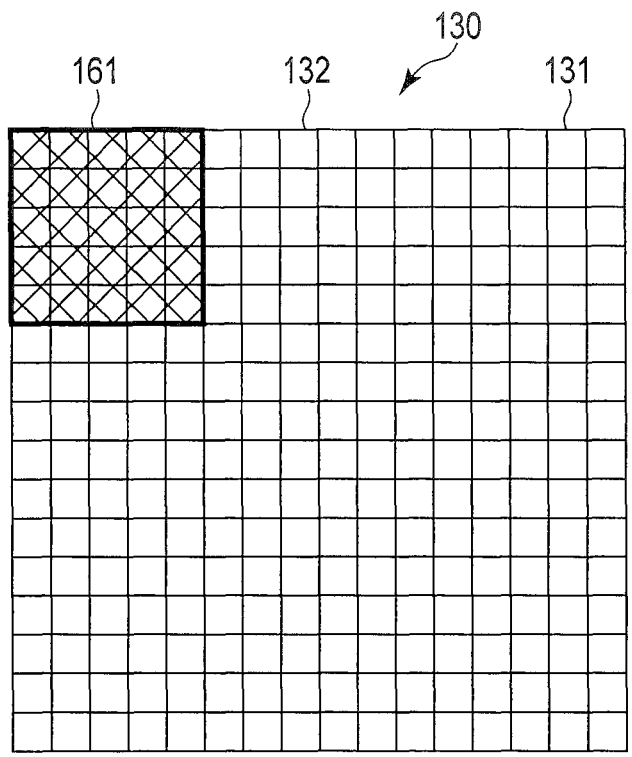
FIG. 5A is a diagram schematically showing a light receiving surface of a monochrome CCD as an image sensor.
Figure 5B:
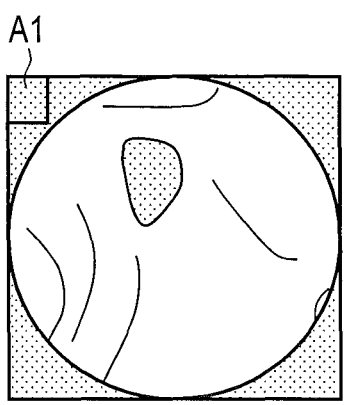
FIG. 5B is a diagram schematically showing an example of an observation object image acquired by the image sensor of FIG. 5A.

The measurement light receiving section 161 may use three or more color filters, or use a spectroscope other than the filters. FIG. 5A is a diagram schematically showing a light receiving surface of a monochrome CCD as the image sensor 131. FIG. 5B is a diagram schematically showing a corresponding observation object image. A reflected light receiving section 132 and a measurement light receiving section 161 are also provided on the light receiving surface of the monochrome CCD as the image sensor 131. In the case of the monochrome CCD, measurement light information is acquired by, for example, sequentially turning on a plurality of laser lights that form an illumination light.

(Received Light Information Distribution Circuit)

The received light information distribution circuit 150 is connected to the imager 130 through the imaging cable 220. The received light information distribution circuit 150 separates the electric signals output from the image sensor 131 into the electric signal including reflected light information acquired by the reflected light receiving section 132 and the electric signal including measurement light information acquired by the measurement light receiving section 161, and separately outputs the reflected light information to the image processing circuit 200 and the measurement light information to the color component ratio calculation circuit 162.

(Color Component Ratio Measurement Section (Color Component Ratio Calculation Circuit))

The color component ratio calculation circuit 162 and the measurement light receiving section 161 form the color component ratio measurement section 160 as described above. The measurement light information acquired by the measurement light receiving section 161 is transmitted to the color component ratio calculation circuit 162. The color component ratio calculation circuit 162 calculates a color component ratio of the illumination light based on the measurement light information. Furthermore, the color component ratio calculation circuit 162 outputs the calculated color component ratio information of the illumination light to the light quantity ratio adjustment circuit 170. "Color component ratio" in the present embodiment refers to a ratio of light quantities (pixel values in the present embodiment) in at least three wavelength regions of a red region, a green region, and a blue region. "Color component ratio" also includes a ratio of light quantities in a case of color regions other than the aforementioned three color regions, that is, four or more color regions.

If the measurement light which falls on the measurement light receiving section 161 does not uniformly fall on the aforementioned three color filters, the color component ratio calculation circuit 162 calculates a ratio of the color components of the illumination light in consideration of the ratio of the measurement lights which fall on the respective color filters.

If the color of the illumination light emitted from the optical converter 190 varies depending on light distribution (if there is color unevenness), the illumination light and the measurement light will be different in color component ratio. In such a case, based on a difference between the color component ratio of the measurement light and that of the illumination light obtained in advance, the color component ratio calculation circuit 162 calculates a color component ratio of the illumination light from the color component ratio of the measurement light.

(Measurement Light Guide Section)

The measurement light guide section 140 is arranged at the distal end of the insertion section 20. The measurement light guide section 140 branches a part of the illumination light emitted from the illumination section 120 as a measurement light, while maintaining the color component ratio. The branched light is directly guided to the measurement light receiving section 161, not via the observation object, i.e., without being reflected by the observation object.

FIG. 6 is a diagram schematically showing an optical path of a measurement light at the distal end of the insertion section 20 in the present embodiment. FIG. 7 is a diagram schematically showing a measurement light which falls on the light receiving surface of the image sensor 131. As shown in FIG. 6, a part of an illumination light A2 that is externally emitted from the optical converter 190 and has a wide light distribution angle is used as the measurement light. The optical converter 190 is designed so that the illumination light A2 emitted therefrom is sufficiently wide. As a result, the observation object is radiated with satisfactory light distribution.

The measurement light guide section 140 comprises an optical fiber 141, a first mirror 142, a second mirror 143, a collimate lens 144, and a condenser lens 145. In an optical path of the measurement light at the distal end of the insertion section 20, the first mirror 142, the optical fiber 141, the collimate lens 144, the second mirror 143, and the condenser lens 145 are arranged in this sequence from the optical converter 190 toward the imager 130.

The optical fiber 141, the first mirror 142, the second mirror 143 and the collimate lens 144 are arranged on the distal end surface of the insertion section 20. The first mirror 142 is arranged at a predetermined angle with respect to the distal end surface of the insertion section 20, so as to reflect a measurement light A3 being a part of the illumination light emitted from the optical converter 190, and to guide it to the optical fiber 141. The second mirror 143 is arranged at a predetermined angle with respect to the distal end surface of the insertion section 20, so as to reflect the measurement light A3, which has been guided through the optical fiber 141 and converted to a parallel light by the collimate lens 144, and to guide it to the insertion section 20 again. The condenser lens 145 is arranged in the distal rigid portion 21 of the insertion section 20. The condenser lens 145 condenses the measurement light A3 converted into the parallel light, and causes it to fall on the measurement light receiving section 161, as shown in FIG. 7.

The measurement light guide section 140 is designed to cause the measurement light to be uniformly fell on at least one set of RGB color filters of the measurement light receiving section 161, so that color component ratio measurement can be performed with high accuracy. For example, it uses the optical fiber 141 having a cross-sectional area sufficiently larger than the one set of RGB color filters of the measurement light receiving section 161.

(Light Quantity Ratio Adjustment Circuit)

The light quantity ratio adjustment circuit 170 adjusts a light quantity ratio of laser lights based on the color component ratio of the illumination light output from the color component ratio calculation circuit 162 of the color component ratio measurement section 160, thereby performing color correction of the illumination light emitted from the illumination section 120. The light quantity ratio of the lasers 181a to 181d may change, for example, due to a change in temperature of lasers, in which case the color of the illumination light may change. At that time, the color of the illumination light is corrected to a desired color. This is called color correction.

The light quantity ratio adjustment circuit 170 comprises a storage circuit 171. The storage circuit 171 stores an appropriate color component ratio of the measurement light obtained when the illumination light has the desired color as mentioned above in each of the observation modes. The light quantity ratio adjustment circuit 170 performs light quantity ratio adjustment based on the observation mode information output from the input circuit 110 and the appropriate color component ratio stored in the storage circuit 171.

The appropriate color component ratio is determined as follows: for example, the light quantity ratio of laser lights respectively emitted from the lasers 181a to 181d is set so that the illumination light has a desired color, and the color component ratio of the measurement light at that time is measured in advance. The color component ratio at that time is stored in the storage circuit 171 as the appropriate color component ratio.

If the light quantity ratio of the lasers 181a to 181d changes due to a change in temperature or the like, not only the color, but also the light quantity of the illumination light will change. The light quantity of the illumination light also changes due to the light quantity ratio adjustment described above. Light quantity correction due to these changes is carried out between the image processing circuit 200 and the light source driving circuit 121 in a conventional manner, based on photometry for an observation object image (in FIG. 2, a signal line between the image processing circuit 200 and the light source driving circuit 121 is omitted). At that time, light quantity ratio adjustment is carried out, while the color component ratio is maintained.

In the light quantity ratio adjustment, for example, a laser light quantity of the third laser 181c that emits a green laser light is fixed, and the color component ratio of the measurement light is set to an appropriate color component ratio with reference to the fixed laser light quantity. Alternatively, the color component ratio of the measurement light is set to an appropriate color component ratio so that the light quantity to be adjusted can be minimal.

Processes in the received light information distribution circuit 150, the color component ratio calculation circuit 162 of the color component ratio measurement section 160, and the light quantity ratio adjustment circuit 170 can be executed by a processor including a hardware configuration. For example, those processes can be executed by a processor comprising an electronic circuit such as an ASIC (Application Specific Integrated Circuit). Alternatively, those processes may be executed by reading various programs by a general-purpose processor such as a CPU (Central Processing Unit).

(Image Processing Circuit)

The image processing circuit 200 generates an observation object image through known image processing based on reflected light information output from the received light information distribution circuit 150, and observation mode information output from the input circuit 110.

(Image Display)

The image display 300 displays an observation object image generated by the image processing circuit 200. The image display 300 is, for example, a monitor such as a liquid crystal display.

(Operations and Functions of Endoscope System)

Operations and functions of the endoscope system 1 of the first embodiment will be explained.

When the user inputs an observation mode to the input circuit 110, observation mode information is transmitted from the input circuit 110 to the light source driving circuit 121. Then, a control signal corresponding to the observation mode information is transmitted from the light source driving circuit 121 to the light source 180. In the normal light observation mode, the light source driving circuit 121 turns on the second laser 181b (the blue laser light), the third laser 181c (the green laser light), and the fourth laser 181d (the red laser light). In the specific light observation mode, the light source driving circuit 121 turns on the first laser 181a (the violet laser light) and the third laser 181c (the green laser light). The light quantity ratio of the lasers 181a to 181d at this time follows current values to be input to the lasers that are set in advance to make the illumination light be a desired color.

In each of the observation modes, a plurality of laser lights are mixed by optical combiner 183. Thereafter, the mixed light is guided through the optical fiber 122 and transmitted to the optical converter 190. The transmitted light is diffused by the optical diffuser 191 of the optical converter 190 to expand the light distribution, and emitted through an illumination window (not shown) to the observation project as an illumination light.

Most of the emitted illumination light is radiated on the observation object, and reflected by the observation object. Then, the reflected light falls on the reflected light receiving section 132 of the imager 130 from the observation optical system 210. The light reflected by the observation object does not fall on the measurement light receiving section 161. The reflected light information acquired by the reflected light receiving section 132 is transmitted to the image processing circuit 200 via the received light information distribution circuit 150. Then, the image processing circuit 200 generates an observation object image, and the image display 300 displays the observation object image.

On the other hand, part of the emitted illumination light is directly guided to the measurement light guide section 140 as a measurement light, not via the observation object. Then, the measurement light falls on the measurement light receiving section 161 from the measurement light guide section 140. In other words, after the measurement light is emitted from the optical converter 190, it is not radiated on the observation object, but returns inside the insertion section 20 through the measurement light guide section 140, and is received by the measurement light receiving section 161. The measurement light does not fall on the reflected light receiving section 132. Furthermore, the measurement light is not used for generation of an observation object image. The measurement light information acquired by the measurement light receiving section 161 is transmitted to the color component ratio calculation circuit 162 via the received light information distribution circuit 150. Furthermore, the color component ratio calculation circuit 162 calculates a color component ratio of the measurement light, and outputs the calculated color component ratio information of the illumination light to the light quantity ratio adjustment circuit 170.

The light quantity ratio adjustment circuit 170 outputs to the light source driving circuit 121 a control signal to adjust the light quantities (light quantity ratio) of the laser lights respectively emitted from the lasers 181a to 181d, so as to make the light component ratio of the illumination light equal to the appropriate light component ratio stored in the storage circuit 171. As described above, the light quantities of the respective lasers 181a to 181d are adjusted so that the color component ratio of the measurement light (illumination light) can be an appropriate color component ratio by fixing the light quantity of one laser and making the color component ratio of the measurement light equal to the appropriate color component ratio with reference to the fixed light quantity, or by making the light quantity to be adjusted be minimal. Light quantity correction of the illumination light is also performed between the image processing circuit 200 and the light source driving circuit 121, as described above, in a conventional manner based on the photometry for the observation object image while maintaining the color component ratio. Such correction is always repeatedly performed during operation of the endoscope system 1.

Advantageous Effect

According to the present embodiment, a color change of the illumination light can be corrected by the color component ratio measurement section 160 that measures a color component ratio of the illumination light made of a mixed light of a plurality of narrow-band lights (e.g., laser lights) in cooperation with the light quantity ratio adjustment circuit 170 that adjusts the light quantity ratio of the narrow-band lights as the illumination light. Therefore, it is possible to provide the endoscope system 1 in which, even if the quantities of laser lights are changed due to a change in temperature of the lasers, the change can be corrected and observation under the illumination light of a desired color can be performed.

Furthermore, due to the use of lasers 181a to 181d as a light source, efficient light coupling and light guide for a thin optical fiber is possible. Accordingly, bright illumination can be provided, while the diameter of the insertion section is reduced.

Moreover, in the present embodiment, a part of the existing imager 130 of the endoscope 10, for example, a pixel area of the existing image sensor 131 not used for generation of an observation object image, is used as the measurement light receiving section 161 of the color component ratio measurement section 160. Therefore, it is unnecessary to add a new light receiving section for color component measurement. Accordingly, the production cost can be reduced as compared to a case where a new light receiving section is added. Furthermore, the imager 130 can generate an observation object image in a conventional manner, even if the measurement light receiving section 161 is provided.

In the present embodiment, since the measurement light guide section 140 is provided, part of the illumination light can be guided to the measurement light receiving section 161 as the measurement light without changing the color components before the illumination light is radiated on the observation object. Therefore, the color component of the illumination light can be measured without any influence of the observation object.

In the present embodiment, light quantity ratio adjustment is performed using an appropriate color component ratio stored in the storage circuit 171 of the light quantity ratio adjustment circuit 170. As a result, appropriate color correction to illumination light of a desired color is possible. Furthermore, since the storage circuit 171 stores an appropriate color component ratio corresponding to each observation mode, color correction of illumination light during observation is possible even in different observation modes.

In the present embodiment, the optical fiber 141 is used in the measurement light guide section 140. Accordingly, the measurement light can be guided efficiently in a small space. Also, the condenser lens 145 is used in the measurement light guide section 140, and the measurement light is condensed by the condenser lens 145 in the measurement light receiving section 161. Accordingly, even a small measurement light receiving section 161, it enables the measurement light to fall on the section.

Variants 1 to 3 of the first embodiment and a second embodiment will be explained below. In the following, the same reference symbols as used in the first embodiment will be used for the same parts, and detailed explanations thereof will be omitted.

[Variant 1]

Figure 8:
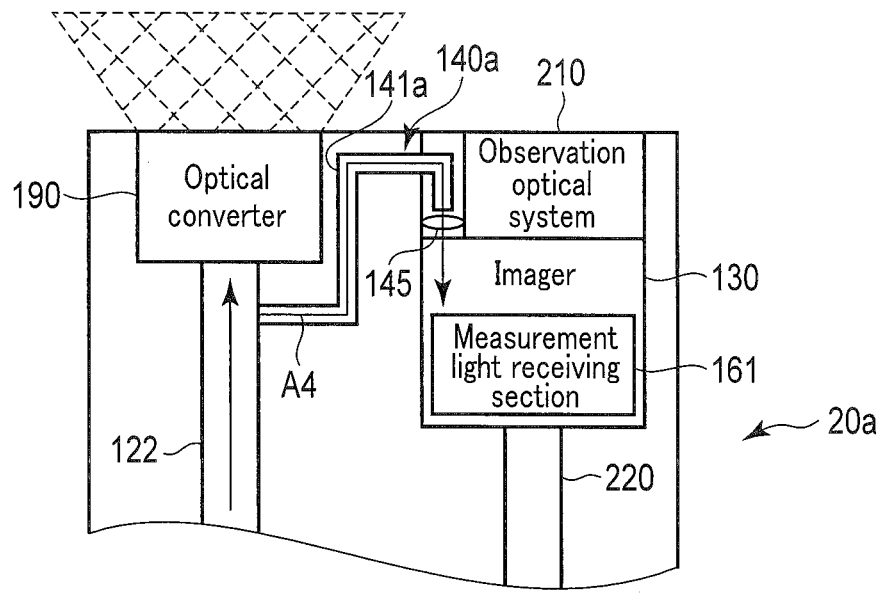
FIG. 8 is a diagram schematically showing an optical path of a measurement light at a distal end of an insertion section in Variant 1 of the first embodiment.

FIG. 8 is a diagram schematically showing an optical path of a measurement light at a distal end of an insertion section 20a in Variant 1. In present variant, a measurement light guide section 140a is arranged inside the insertion section 20a. The measurement light guide section 140a comprises an optical fiber 141a branched from an optical fiber 122, and a condenser lens 145. For example, the branching optical fiber 141a is fused to the optical fiber 122, thereby forming an optical fiber coupler which serves as a measurement light branch. In the variant, part of an illumination light guided through the optical fiber 122 is guided to the optical fiber 141a as a measurement light 4A, not via an optical converter 190, condensed by the condenser lens 145, and falls on a measurement light receiving section 161.

In present variant, the optical fiber 141a and the condenser lens 145 that form the measurement light guide section 140a is arranged inside the insertion section 20a. Thus, the measurement light guide section 140a does not protrude from a distal end surface of the insertion section 20a. Therefore, it is possible to avoid a load due to contact between the measurement light guide section 140a and an observation object, or deterioration due to a contact between the measurement light guide section 140a and a body fluid or the like in a living body.

Furthermore, in the variant, the measurement light guide section 140a does not use a mirror or a collimate lens. Thus, in the present variant, the measurement light can be guided to the measurement light receiving section 161 with less members as compared to the first embodiment.

[Variant 2]

Figure 9:
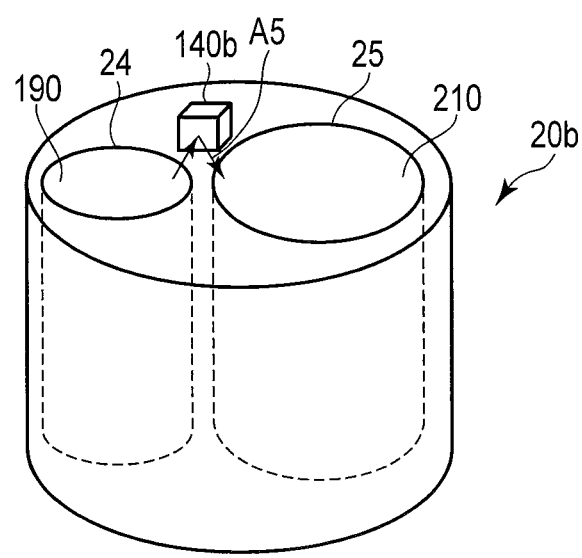
FIG. 9 is a diagram schematically showing a distal end of an insertion section in Variant 2 of the first embodiment.

FIG. 9 is a diagram schematically showing a distal end of an insertion section 20b in Variant 2. A window of an optical converter 190 as an illumination window 24 and a window of an observation optical system 210 as an observation window 25 are provided in a distal end surface of the insertion section 20b. Furthermore, in the present variant, a measurement light guide section 140b is provided on the distal end surface of the insertion section 20b. The measurement light guide section 140b is, for example, a reflection plate having a known reflection spectrum.

Part of an illumination light emitted from the illumination window 24 is reflected by the measurement light guide section 140b and received by a measurement light receiving section 161 through the observation window 25. This part of light is referred to as a measurement light A5. In the present variant, the position and angle of the reflection plate of the measurement light guide section 140b are set and the observation optical system 210 is designed so that the measurement light A5 directly falls on the measurement light receiving section 161, but does not fall on a reflected light receiving section 132. Furthermore, the observation optical system 210 is designed so that a reflected light from the observation object does not fall on the measurement light receiving section 161.

Figure 10:
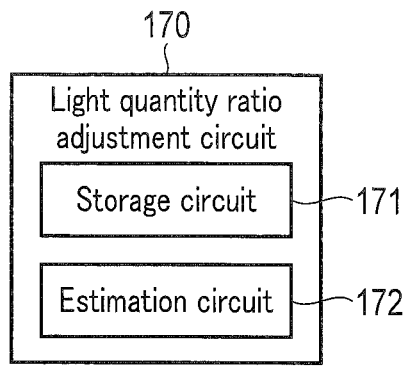
FIG. 10 is a block diagram showing an example of a light quantity ratio adjustment circuit in Variant 2.

FIG. 10 is a block diagram showing an example of a light quantity ratio adjustment circuit 170b in Variant 2. The light quantity ratio adjustment circuit 170b comprises a storage circuit 171 and an estimation section 172. If the reflectivity of the reflection plate of the measurement light guide section 140b has wavelength dependence, a measurement light and an illumination light are different in color composition ratio. As described above, the reflection spectrum of the reflection plate is known. Therefore, in the present variant, the estimation section 172 estimates a color composition ratio of the illumination light from the color component ratio of the measurement light and the reflection spectrum of the reflection plate. Thus, "measurement light" in the present variant includes a guided light having a color component ratio different from that of an illumination light, where the color component ratio of the illumination light can be estimated.

Figure 11:
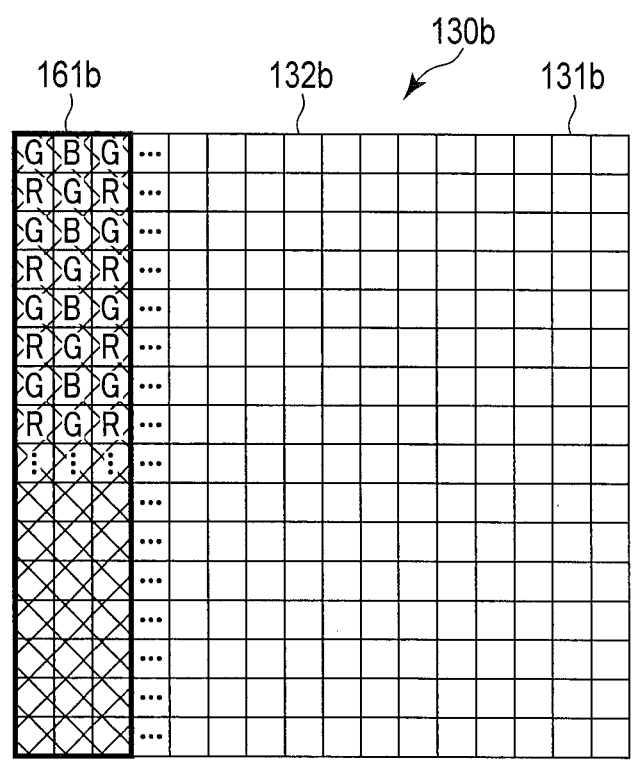
FIG. 11 is a diagram schematically showing an example of a light receiving surface of an image sensor in Variant 2.

FIG. 11 is a diagram schematically showing an example of a light receiving surface of an image sensor 131b in Variant 2. In the present variant, a light receiving surface of the image sensor 131b includes a measurement light receiving section 161b that is a pixel area arranged in a line at one end of the light receiving surface, and a reflected light receiving section 132b that is a pixel area different from the measurement light receiving section 161b.

According to the variant, the reflection plate having a known reflection spectrum is arranged as the measurement light guide section 140b on the distal end surface of the insertion section 20b, so that neither a condenser lens nor an optical fiber need be used in the measurement light guide section 140b.

Thus, in the present variant, the measurement light can be guided to the measurement light receiving section 161b with the minimum number of members.

[Variant 3]

Figure 12:
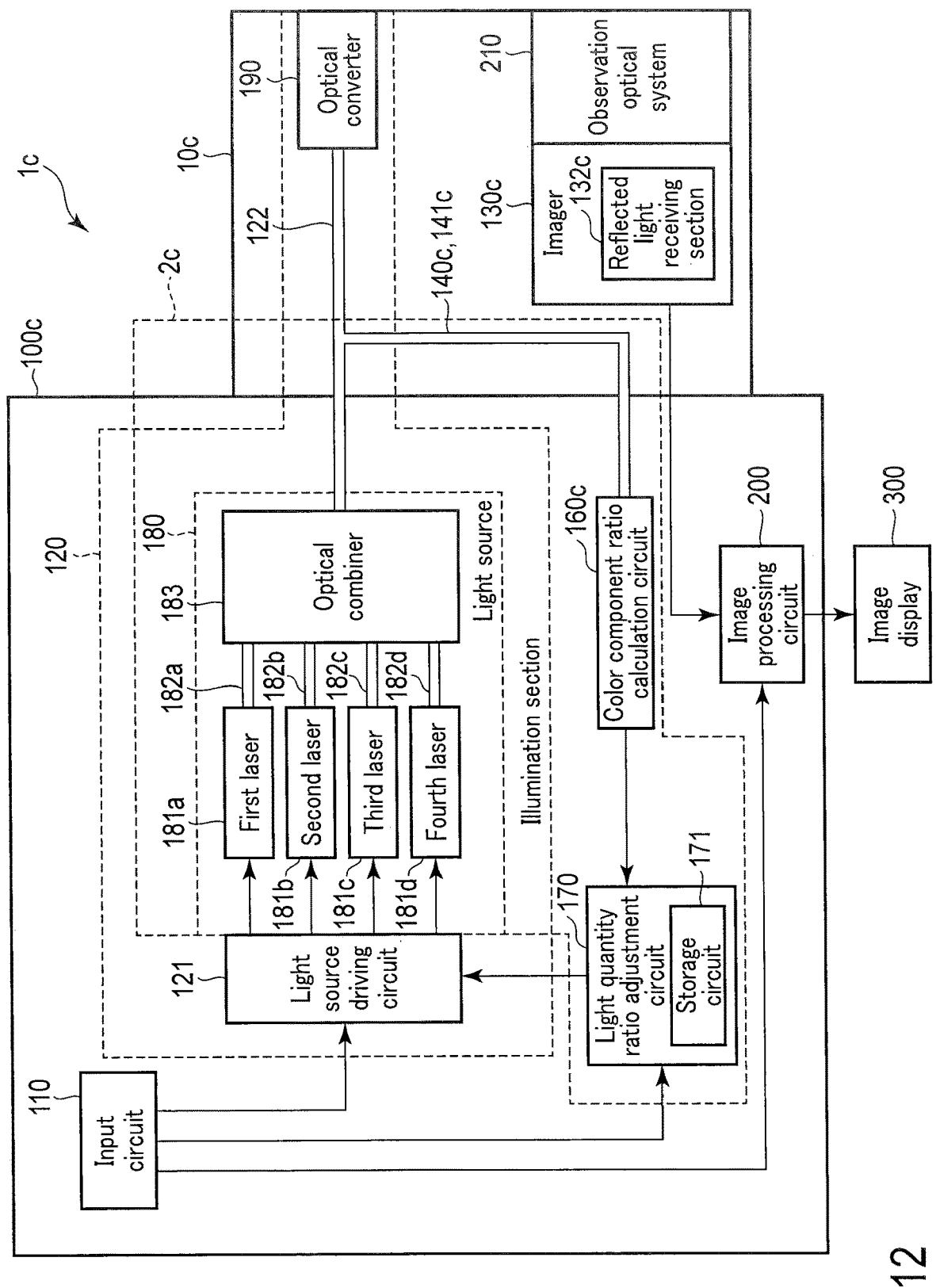
FIG. 12 is a block diagram showing a main configuration of an endoscope system of Variant 3 of the first embodiment.

FIG. 12 is a block diagram showing a main configuration of the endoscope system 1 of Variant 3. In the present variant, a light receiving surface of an image sensor of an imager 130c includes only a reflected light receiving section 132c. In other words, the imager 130c does not comprise a measurement light receiving section that forms a color component ratio measurement section. Thus, the imager 130c is a conventional imager, which is not involved in color component ratio measurement. The imager 130c is connected to an image processing circuit 200 through an imaging cable. A color component ratio measurement section 160c is provided independent of the imager 130c and arranged in a main body 100c.

A measurement light guide section 140c comprises an optical fiber 141c branched from an optical fiber 122 in an endoscope 10c. In the same manner as Variant 1, the branching optical fiber 141c is fused to the optical fiber 122, for example, thereby forming an optical fiber coupler which serves as a measurement light branch. A distal end of the optical fiber 141c is optically connected to a color component ratio measurement section 160c. The optical fiber 141c guides part of an illumination light guided through the optical fiber 122 as a measurement light to the color component ratio measurement section 160c, not via an optical converter 190 and the imager 130c.

According to the variant, an optical system of a measurement light guide section need not be arranged on the distal rigid portion of the insertion section provided with the imager. Therefore, the distal rigid portion can be designed to save space. According to the present variant also, the measurement light can be guided to the color component ratio measurement section 160c with less members as compared to the first embodiment.

In the present variant, the imager 130c is not involved in color correction of an illumination light. Therefore, according to the present variant, a change in color of an illumination light made of a plurality of narrow-band lights can be corrected by an endoscope light source apparatus 2c comprising a light source 180, the color component ratio measurement section 160c, and a light quantity ratio adjustment circuit 170. As a result, observation under the illumination light of a desired color can be performed.

Second Embodiment

Figure 13:
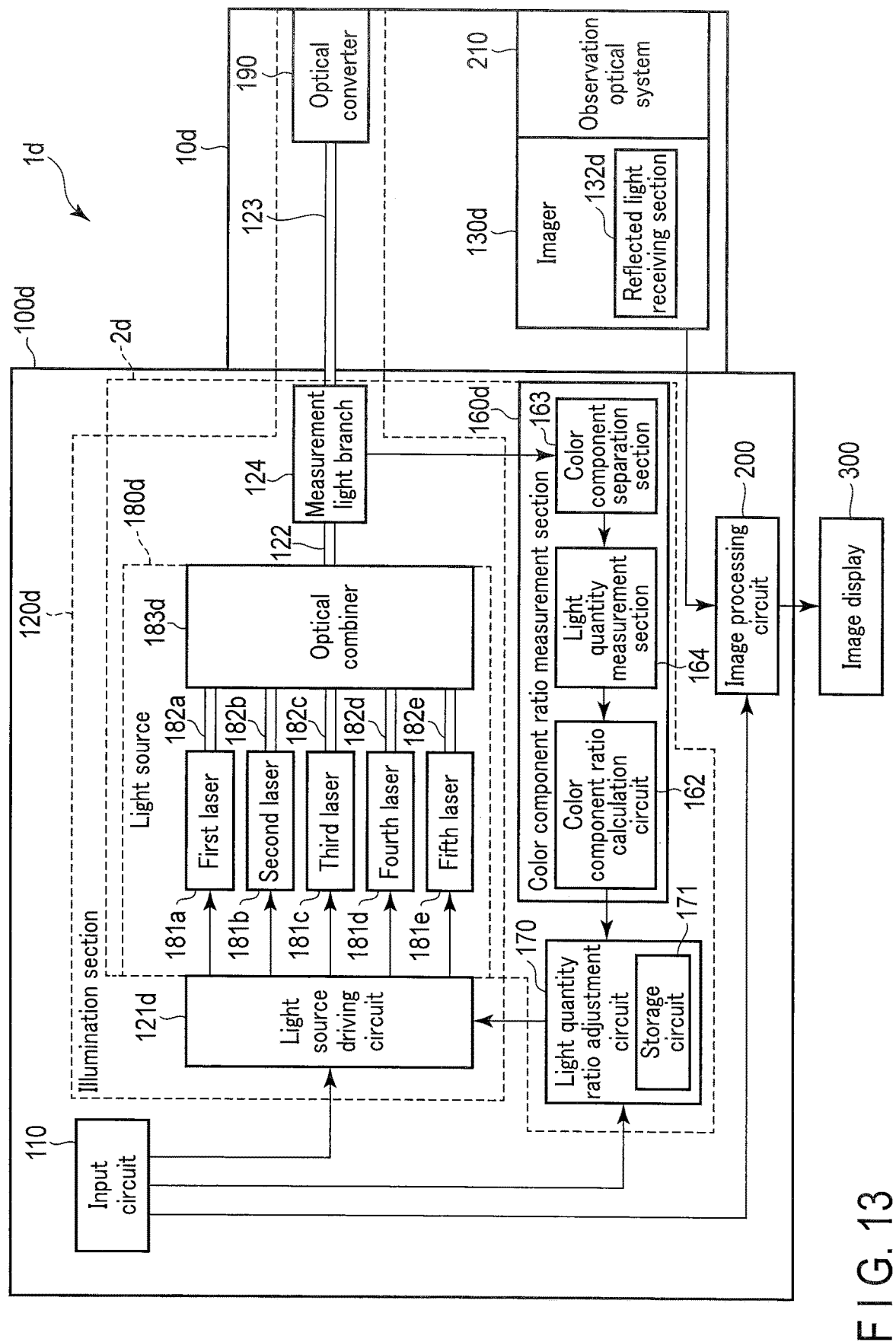
FIG. 13 is a block diagram showing a main configuration of an endoscope system of a second embodiment.

FIG. 13 is a block diagram showing a main configuration of an endoscope system 1d of a second embodiment. The endoscope system 1d comprises an input circuit 110, an illumination section 120d, an imager 130d, a color component ratio measurement section 160d, a light quantity ratio adjustment circuit 170, an image processing circuit 200, and an image display 300. The input circuit 110, the color component ratio measurement section 160d, the light quantity ratio adjustment circuit 170, and the image processing circuit 200 are arranged in a main body 100d. The illumination section 120d is arranged ranging from an endoscope 10d to the main body 100d. The imager 130 is arranged in the endoscope 10d.

(Illumination Section)

The illumination section 120d comprises a light source 180d, a light source driving circuit 121d, optical fibers (illumination light guide sections) 122 and 123, a measurement light branch 124, and an optical converter 190. The light source 180d and the optical converter 190 are optically connected through the optical fibers 122 and 123 and the measurement light branch 124.

(Light Source)

In the present embodiment, the light source 180d comprises a fifth laser 181e in addition to first to fourth lasers 181a to 181d. The fifth laser 181e is a laser that radiates an orange laser light, for example, a diode pumped solid-state (DPSS) laser having a center wavelength of 595 nm. The fifth laser 181e is also connected to the light source driving circuit 121d, and the driving is controlled by the light source driving circuit 121d.

The light source 180d comprises a fifth optical fiber 182e in addition to first to fourth optical fibers 182a to 182d. The fifth optical fibers 182e is also a solid fiber having a core diameter of, for example, several μm to several hundreds of μm. A proximal end of the fifth optical fiber 182e is optically connected to the fifth laser 181e. A distal end of the fifth optical fiber 182e is optically connected to an optical combiner 183d. A proximal end of the optical fiber 122 is optically connected to the optical combiner 183d.

The fifth optical fiber 182e guides a laser light from the fifth lasers 181e. The optical combiner 183d combines the laser lights guided through the first to fifth optical fibers 182a to 182e. The optical fiber 122 guides the light combined by the optical combiner 183 to the optical converter 190 through the measurement light branch 124 and an optical fiber 123. An optical coupling lens (not shown) is arranged also between the fifth laser 181e and the fifth optical fiber 182e to converge the laser light emitted from the fifth laser 181e and couple it to the fifth optical fiber 182e.

(Light Source Driving Circuit)

The light source driving circuit 121d turns on the first to fifth lasers 181a to 181e based on observation mode information output from the input circuit 110. In the present embodiment, when the normal light observation mode is input to the input circuit 110, the second laser 181b (a blue laser light), the third laser 181c (a green laser light), the fourth laser 181d (a red laser light), and the fifth laser 181e (an orange laser light) are simultaneously turned on. Alternatively, the first laser 181a (a violet laser light) may be turned on. When the specific light observation mode is input to the input circuit 110, the first laser 181a (a violet laser light) and the third laser 181c (a green laser light) are simultaneously turned on in the same manner as the first embodiment.

(Measurement Light Branch)

Figure 14:
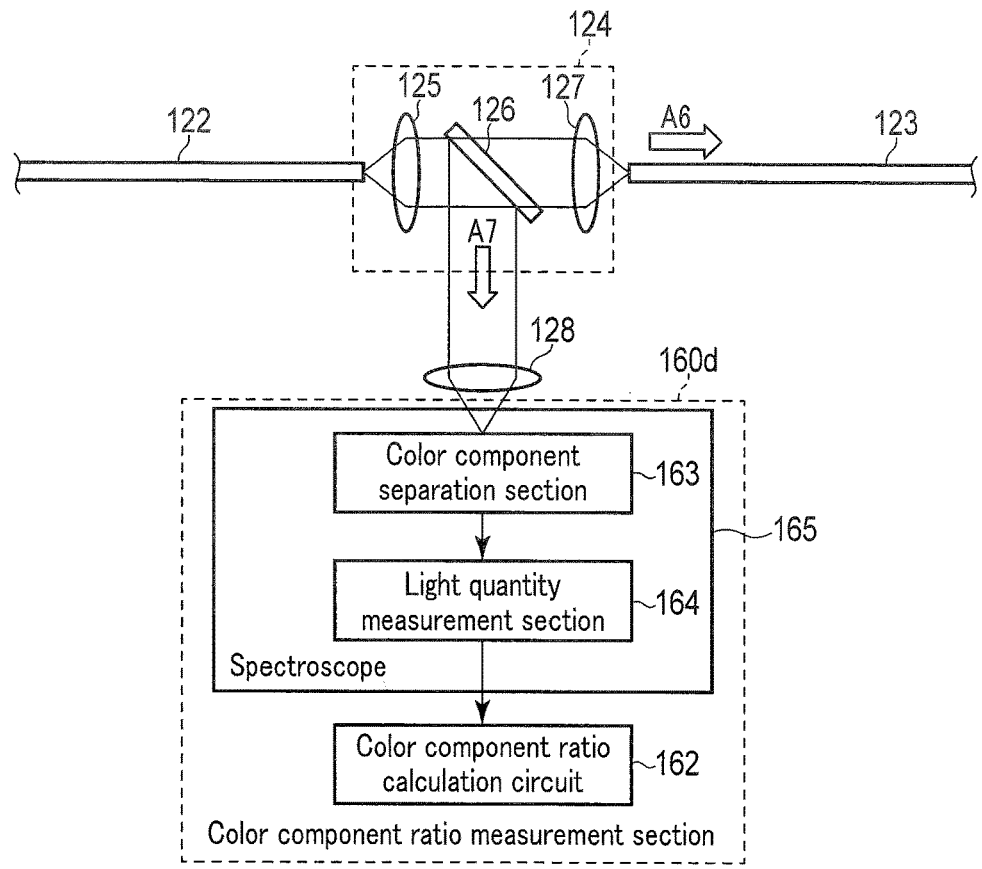
FIG. 14 is a diagram schematically showing an example of a measurement light branch and a color component ratio measurement section in the second embodiment.

FIG. 14 is a diagram schematically showing an example of the measurement light branch 124 and the color component ratio measurement section 160d. The measurement light branch 124 corresponds to the measurement light guide section of the first embodiment, and is provided to branch part of the illumination light and to guide the branched light to the color component ratio measurement section 160d as a measurement light, not via an observation object, while maintaining the color composition ratio. The measurement light branch 124 is arranged between the optical fiber (first light guide) 122 and the optical fiber (second light guide) 123 in an optical path of the illumination light from the light source 180d to the optical converter 190. The measurement light branch 124 comprises a collimate lens 125, a beam splitter 126, and a condenser lens 127. The collimate lens 125, the beam splitter 126, and the condenser lens 127 are arranged in the optical path between the light source 180d and the optical converter 190 in this sequence. In other words, the beam splitter 126 is arranged in the optical path between the collimate lens 125 and the condenser lens 127.

The collimate lens 125 converts the illumination light emitted from the optical fiber 122 to a parallel light. The beam splitter 126 is arranged at a predetermined angle with respect to a direction of the optical path of the illumination light, so as to transmit most part of the parallel converted-illumination light, reflect a light A7, which is a part of the illumination light, and guide the reflected light to the color component ratio measurement section 160d. The condenser lens 127 condenses the illumination light transmitted through the beam splitter 126 and makes it fell in the optical fiber 123.

The part of the illumination light reflected by the beam splitter 126 is condensed by a condenser lens 128 and guided to the color component ratio measurement section 160d as the measurement light A7 to measure the color component ratio of the illumination light. The ratio of the measurement light A7 guided to the color component ratio measurement section 160d is smaller than the ratio of the illumination light A6 guided to the optical fiber 123. The light quantity of the measurement light A7 guided to the color component ratio measurement section 160d is preferably 10% or less, and is more preferably 1% or less of the light quantity of the illumination light A6 guided to the optical fiber 123.

Figure 15:
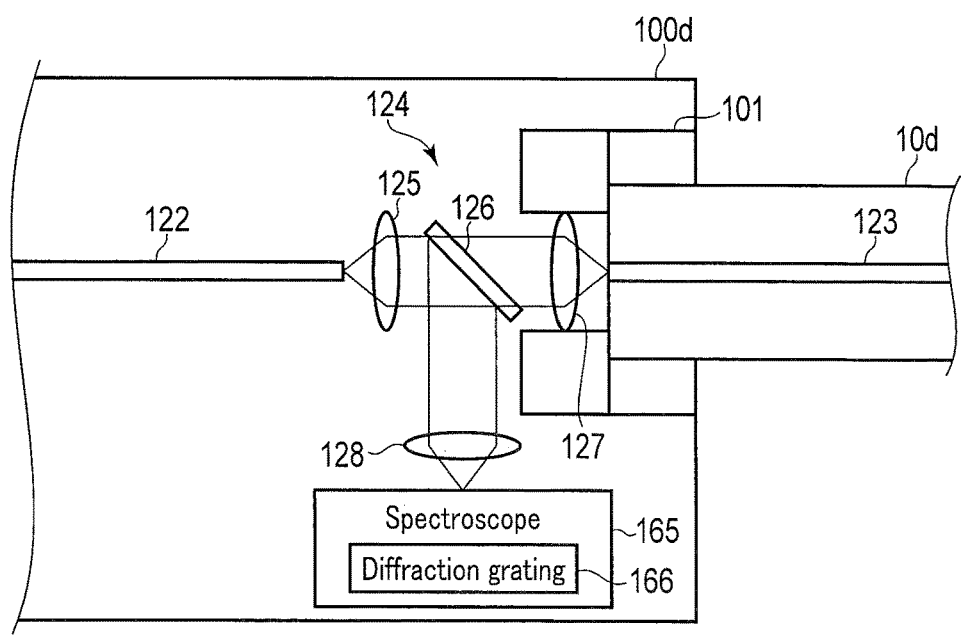
FIG. 15 is a diagram schematically showing an example of a connection between a main body and an endoscope.
Figure 18:
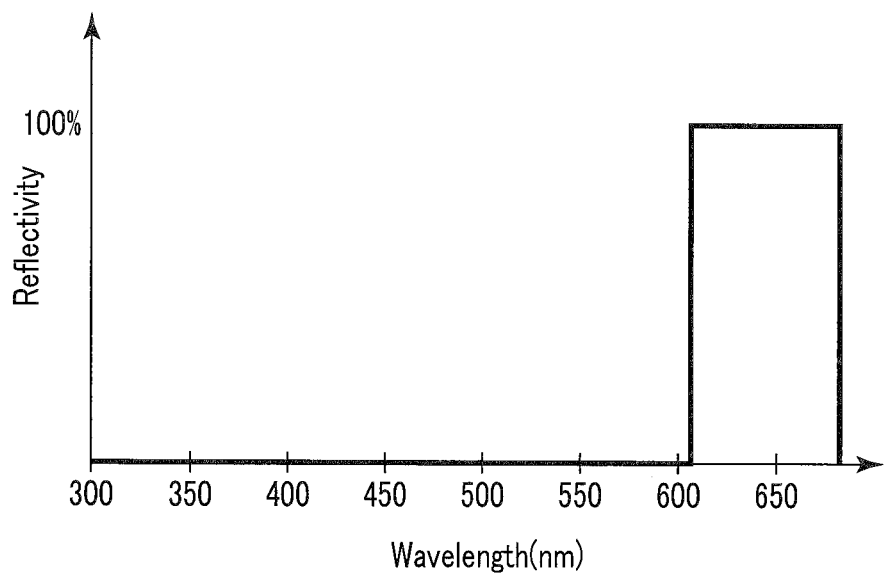
FIG. 18 is a diagram showing an example of a relationship between a wavelength and a reflectivity in a first dichroic mirror of a color component separation section.
Figure 19:
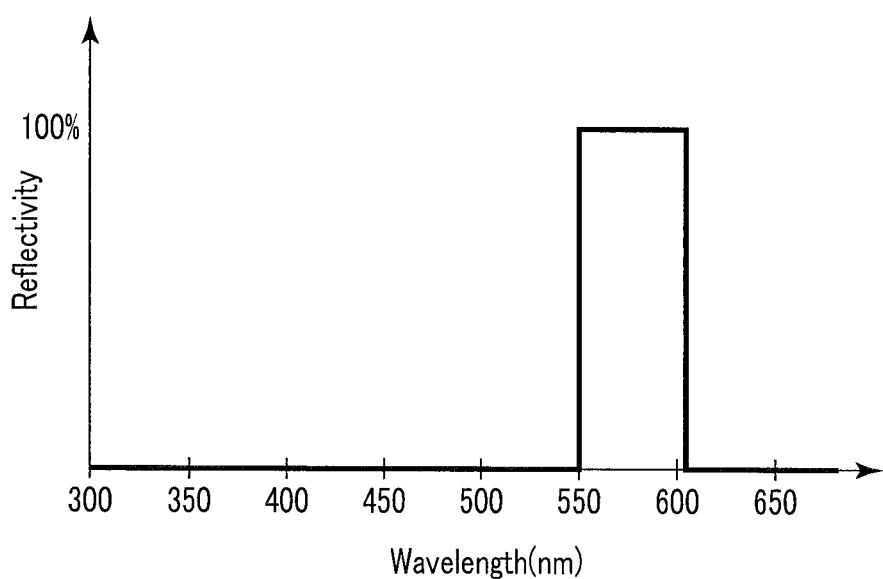
FIG. 19 is a diagram showing an example of a relationship between a wavelength and a reflectivity in a second dichroic mirror of the color component separation section.

In the present embodiment, the optical combiner 183d, the optical fiber 122, the measurement light branch 124, and the color component ratio measurement section 160d are arranged in the main body 100d. The optical fiber 123 is arranged in the endoscope 10d detachably connected to the main body 100d. For example, as shown in FIG. 15, the condenser lens 127 of the measurement light branch 124 is arranged in a connector 101 that detachably connects the endoscope 10d to the main body 100d. When the main body 100d and the endoscope 10d are connected to each other, the condenser lens 127 in the main body 100d side and the optical fiber 123 on the endoscope 10d side are optically aligned, so that the illumination light is guided through the optical fiber 123.

Generally, in the connector 101, the illumination light is taken out from the optical fiber 122 into space to adjust the incident angle with respect to the endoscope 10d. In the present embodiment, the measurement light branch 124 is provided in an area including the space, into which the illumination light is taken out, to branch part of the illumination light. As a result, the illumination light can be efficiently guided.

In the present embodiment, the collimate lens 125, the beam splitter 126, and the condenser lens 127 are used as the measurement light branch 124. However, the light guided through the optical fiber 122 may be branched in the same manner as in Variants 1 and 3 of the first embodiment. For example, as shown in FIG. 16, an optical fiber coupler may be used as the measurement light branch 124. For example, the optical fiber coupler is produced by fusing a branching optical fiber 129 to the optical fiber 122. The optical fiber coupler is also designed so that the illumination light A7 of 10% or less, more preferably 1% or less of the light quantity of the illumination light guided through the optical fiber 122, is branched to the optical fiber 129 as the measurement light. The configuration that does not take the measurement light A7 out of the optical fiber 122 into space is effective for downsizing the measurement light branch 124.

(Imager)

An imager 130d is a conventional imager, which is not involved in color component ratio measurement and comprises a reflected light receiving section 132d for acquiring an observation body image, as well as Variant 3 of the first embodiment. The imager 130d is connected to the image processing circuit 200 through an imaging cable.

(Color Component Ratio Measurement Section)

In the present embodiment, the color component ratio measurement section 160d comprises a color component separation section 163, a light quantity measurement section 164, and a color component ratio calculation circuit 162. The color component separation section 163 is optically connected to the measurement light branch 124 of the illumination section 120d. The color component separation section 163 separates the measurement light branched from the illumination light by the measurement light branch 124 into each of the narrow-band lights being independent of each other. The light quantity measurement section 164 measures a light quantity of each of the narrow-band lights separated by the color component separation section 163, and outputs the measured light quantities to the color component ratio calculation circuit 162. The color component ratio calculation circuit 162 calculates a color component ratio of the measurement light (illumination light) based on the output from the light quantity measurement section 164.

The color component ratio measurement section 160d (the color component ratio calculation circuit 162) outputs the measured (calculated) color component ratio of the illumination light to the light quantity ratio adjustment circuit 170. Color component ratio measurement by the color component ratio measurement section 160d is repeatedly performed during observation of an observation object by the endoscope system 1d, and repeatedly output to the light quantity ratio adjustment circuit 170.

The color component separation section 163 and the light quantity measurement section 164 of the color component ratio measurement section 160d form, for example, a spectroscope 165 as shown in FIGS. 14 and 15 that separates the measurement light into lights of the respective wavelengths. The spectroscope 165 comprises an optical element that is, for example, a diffraction grating 166. The diffraction grating 166 is designed to separate at least the measurement light into each of the narrow-bands lights being independent of each other.

Furthermore, for example, as shown in FIG. 17, a dichroic mirror, which reflects a light of a specific wavelength and transmits lights of the other wavelengths, may be used as the color component separation section 163, and a photodetector (PD) may be used as the light quantity measurement section 164. FIG. 17 shows the color component separation section 163 including a first dichroic mirror 163a, a second dichroic mirror 163b, a third dichroic mirror 163c, a fourth dichroic mirror 163d, and the light quantity measurement section 164 including a first photodetector 164a, a second photodetector 164b, a third photodetector 164c, and a fourth photodetector 164d. Condenser lenses 165a to 165d are respectively arranged between the first to fourth dichroic mirrors 163a to 163d and the first to fourth photodetectors 164a to 164d.

FIG. 18 to FIG. 21 are diagrams respectively showing examples of a relationship between a wavelength and a reflectivity of the first to fourth dichroic mirrors 163a to 163d, in the case where the second laser 181b (the blue laser light), the third laser 181c (the green laser light), the fourth laser 181d (the red laser light), and the fifth laser 181e (the orange laser light) are simultaneously turned on in the normal observation mode. The first dichroic mirror 163a reflects 100% of only the light of, for example, a wavelength of 610 nm to 700 nm. The second dichroic mirror 163b reflects 100% of only the light of, for example, a wavelength of 550 nm to 610 nm. The third dichroic mirror 163c reflects 100% of only the light of, for example, a wavelength of 500 nm to 550 nm. The fourth dichroic mirror 163d reflects 100% of only the light of, for example, a wavelength of 300 nm to 475 nm. For example, the dichroic mirrors 163a to 163d are designed to have the reflectivities with respect to the wavelengths as shown in FIG. 18 to FIG. 21, so that the narrow-band lights can be independently separated.

Specifically, the measurement light A7 branched at the measurement light branch 124 is guided to the first dichroic mirror 163a. The first dichroic mirror 163a reflects only a light of a wavelength of 610 nm to 700 nm. The reflected narrow-band light is condensed by the condenser lens 165a and detected by the first photodetector 164a. The light transmitted through the first dichroic mirror 163a is guided to the second dichroic mirror 163b. The second dichroic mirror 163b reflects only a light of a wavelength of 550 nm to 610 nm. The reflected narrow-band light is condensed by the condenser lens 165b and detected by the second photodetector 164b. The light transmitted through the second dichroic mirror 163b is guided to the third dichroic mirror 163c. The third dichroic mirror 163c reflects only a light of a wavelength of 500 nm to 550 nm. The reflected narrow-band light is condensed by the condenser lens 165c and detected by the third photodetector 164c. The light transmitted through the third dichroic mirror 163c is guided to the fourth dichroic mirror 163d. The fourth dichroic mirror 163d reflects only a light of a wavelength of 300 nm to 475 nm. The reflected narrow-band light is condensed by the condenser lens 165d and detected by the fourth photodetector 164d. Thus, the narrow-band lights are separated by the color component separation section 163, and measured by the light quantity measurement section 164.

The number of dichroic mirrors as the color component separation section 163, the number of photodetectors as the light quantity measurement section 164, and the relationship between a wavelength and a reflectivity are not limited to those mentioned above, but may be set variously within the ranges that allow the narrow-band lights to be independently separated.

(Color Component Ratio Calculation Circuit)

The color component ratio calculation circuit 162 calculates a color component ratio of the illumination light based on the light quantities of the respective color components (the respective narrow-band lights) of the measurement light measured by the light quantity measurement section 164. "Color component ratio" in the present embodiment includes the ratio of the light quantities of the respective narrow-band lights of a plurality of narrow-band lights in addition to the ratio explained for the first embodiment. The color component ratio calculation circuit 162 calculates a color component ratio (a color quantity ratio of the narrow-band lights) also in consideration of a branching ratio of the illumination light and the measurement light in the measurement light branch 124 and wavelength dependence of light guide efficiency. The color component ratio calculation circuit 162 outputs the calculated color component ratio of the illumination light to the light quantity ratio adjustment circuit 170.

(Light Quantity Ratio Adjustment Circuit)

As well as the first embodiment, the light quantity ratio adjustment circuit 170 adjusts a light quantity ratio of a plurality of laser lights based on the color component ratio of the illumination light output from the color component ratio calculation circuit 162 of the color component ratio measurement section 160d, thereby performing color correction of the illumination light emitted from the illumination section 120d. The light quantity of the lasers 181a to 181e may change, for example, due to a change in temperature of the lasers 181a to 181e (the light source 180d) and accordingly the light quantity ratio of the laser lights may change, in which case the color of the illumination light may change. At that time, the color of the illumination light is corrected to a desired color. This is called color correction.

Light quantity ratio adjustment is performed so that the light quantity of one laser, for example, the third laser that emits a green laser light is fixed, and the color component ratio of the measurement light is made equal to an appropriate color component ratio with reference to the fixed light quantity. Alternatively, the color component ratio of the measurement light is set to an appropriate color component ratio so that the light quantity to be adjusted can be minimal.

As described above, color component ratio measurement by the color component ratio measurement section 160d is repeatedly performed during observation of an observation object, and repeatedly output to the light quantity ratio adjustment circuit 170. The light quantity ratio adjustment circuit 170 repeatedly performs adjustment of the light quantity ratio during observation in accordance with the repeated output.

According to the present embodiment, as well as the first embodiment, a color change of the illumination light can be corrected by the color component ratio measurement section 160d that measures a color component ratio of the illumination light made of a mixed light of a plurality of narrow-band lights in cooperation with the light quantity ratio adjustment circuit 170 that adjusts the light quantity ratio of the narrow-band lights as the illumination light. Therefore, it is possible to provide the endoscope system 1 in which, even if the quantities of laser lights are changed due to a change in temperature of the lasers, the change can be corrected and observation under the illumination light of a desired color can be performed.

In the present embodiment, the measurement light branch 124 and the color component ratio measurement section 160d are arranged in the main body 100, and the measurement light is not guided inside the endoscope 10. Therefore, the endoscope 10 can be designed to save space.

Furthermore, the ratio of the measurement light guided to the color component ratio measurement section 160d is set to be smaller than the ratio of the illumination light emitted from the illumination section 120d. As a result, loss of the emitted illumination light can be small and the desired illumination light can be maintained.

The above explanation is made with reference to the endoscope system 1d. In the present embodiment, as well as Variant 3, an endoscope light source apparatus 2d comprising the light source 180d, the color component ratio measurement section 160d, and the light quantity ratio adjustment circuit 170 corrects a color change of the illumination light made of a plurality of narrow-band lights. As a result, observation under the illumination light of a desired color can be performed. Thus, the present embodiment can provide the endoscope light source apparatus 2d in which a color change of the illumination light, resulting from a change of the laser light quantity ratio due to a change in temperature of a laser, can be corrected by the color component ratio measurement section 160d that measures a color component ratio of the illumination light made of a mixed light of a plurality of narrow-band lights in cooperation with the light quantity ratio adjustment circuit 170, which adjusts the light quantity ratio of the narrow-band lights as the illumination light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an illumination section, including a light source, which sequentially or simultaneously radiates an illumination light being a plurality of narrow-band lights having wavelengths different from each other and having light quantities which are independently controllable, on an observation object;
   a color component ratio measurement section which measures a color component ratio of the illumination light;
   a light quantity ratio adjustment circuit which adjusts a light quantity ratio of the narrow-band lights based on an output from the color component ratio measurement section and performs color correction to cause the illumination light to be a desired color;
   an optical combiner which combines the narrow-band lights into the illumination light;
   an illumination light guide which guides the illumination light obtained by combining; and
   a measurement light branch which branches part of the illumination light from the illumination light guide as a measurement light to measure the color component ratio, and guides the measurement light to the color component ratio measurement section, not via the observation object;
   wherein the color component ratio measurement section comprises:
   a color component separation section configured to separate the measurement light into each of the narrow-band lights being independent of each other;

a light quantity measurement section which measures a light quantity of each of the separated narrow-band lights of the respective color components; and a color component ratio calculation circuit which calculates the color component ratio of the illumination light based on an output from the light quantity measurement section.

2. The endoscope system according to claim 1, wherein the color component separation section comprises a spectroscope having a diffraction grating.

3. The endoscope system according to claim 1, wherein the color component separation section comprises a plurality of dichroic mirrors.

4. The endoscope system according to claim 1, wherein a light quantity ratio of the illumination light branched by the measurement light branch to the color component ratio measurement section is smaller than a light quantity ratio of the illumination light guided without being branched.

5. The endoscope system according to claim 1, wherein the measurement light branch comprises a beam splitter which transmits a part of the illumination light and reflects another part of the illumination light.

6. The endoscope system according to claim 5, wherein:
the illumination light guide comprises a first light guide and a second light guide;
the measurement light branch comprises a collimate lens which converts the illumination light emitted from the first light guide to a parallel light, and a condenser lens which causes the illumination light, which has been converted to the parallel light, to fall on the second light guide; and
the beam splitter is arranged in an optical path between the collimate lens and the condenser lens.

7. The endoscope system according to claim 1, comprising an endoscope, and a main body detachably connected to the endoscope, wherein:
the illumination section comprises a light source which emits the illumination light;
the illumination light guide comprises a first light guide and a second light guide;
the measurement light branch guides the illumination light emitted from the first light guide to the second light guide and branches a part of the illumination light to the color component ratio measurement section;
the light source, the optical combiner, the first light guide, the measurement light branch, and the color component ratio measurement section are arranged in the main body; and
the second light guide is arranged in the endoscope.

8. The endoscope system according to claim 6, wherein:
the first light guide and the second light guide are single optical fibers, respectively.

9. The endoscope system according to claim 6, wherein:
the first light guide is single optical fiber; and
the second light guide is a bundle fiber formed of a bundle of a plurality of optical fibers.

10. The endoscope system according to claim 1, comprising a phosphor which is excited by at least one narrow-band light of the narrow-band lights.

11. The endoscope system according to claim 1, comprising an imager which receives a reflected light obtained from the illumination light reflected by the observation object and acquires reflected light information,
wherein the color component ratio measurement section comprises:

a measurement light receiving section which receives a measurement light being a part of the illumination light to acquire measurement light information; and a color component ratio calculation circuit which calculates a color component ratio of the illumination light based on the measurement light information; and a part of the imager is used as the measurement light receiving section.

12. The endoscope system according to claim 11, wherein:
the endoscope system comprises an endoscope, and a main body to be connected to the endoscope; and
the imager and the measurement light receiving section is arranged on the endoscope.

13. The endoscope system according to claim 11, wherein the part of the imager used as the measurement light receiving section is other than an area of the imager which generates an observation object image.

14. The endoscope system according to claim 11, comprising a measurement light guide section which branches a part of the illumination light as the measurement light and guides the measurement light to the measurement light receiving section, not via the observation object.

15. The endoscope system according to claim 14, comprising a received light information distribution circuit which separates and outputs the reflected light information acquired by the imager and the measurement light information,
wherein the output measurement light information is acquired by the color component ratio calculation circuit.

16. The endoscope system according to claim 14, wherein the measurement light guide section comprises an optical fiber to guide the measurement light obtained by branching, and a condenser lens to cause the measurement light to fall on the color component ratio measurement section.

17. The endoscope system according to claim 14, wherein the measurement light guide section comprises a reflection plate having a known reflection spectrum between an observation window which emits the illumination light and the observation object, and the reflected light reflected by the reflection plate directly is caused to fall on the color component ratio measurement section.

18. An endoscope light source apparatus comprising:
a light source which sequentially or simultaneously emits an illumination light being a plurality of narrow-band lights having wavelengths different from each other and having light quantities which are independently controllable;
a color component ratio measurement section which measures a color component ratio of the illumination light; and
a light quantity ratio adjustment circuit which adjusts a light quantity ratio of the narrow-band lights based on an output from the color component ratio measurement section and performs color correction to cause the illumination light to be a desired color;
an optical combiner which combines the narrow-band lights into the illumination light;
an illumination light guide which guides the combined illumination light; and
a measurement light branch which branches a part of the illumination light from the illumination light guide as a measurement light to measure the color component ratio and guides the measurement light to the color component ratio measurement section;

wherein the color component ratio measurement section comprises:
- a color component separation section configured to separate the measurement light into each of the narrow-band lights being independent of each other;
- a light quantity measurement section which measures a light quantity of each of the separated narrow-band lights of the respective color components; and
- a color component ratio calculation circuit which calculates a color component ratio of the illumination light based on an output from the light quantity measurement section.

19. An endoscope system comprising:
an illumination section, including a light source, which sequentially or simultaneously radiates an illumination light being a plurality of narrow-band lights having wavelengths different from each other and having light quantities which are independently controllable, on an observation object;
a color component ratio measurement section which measures a color component ratio of the illumination light;
a light quantity ratio adjustment circuit which adjusts a light quantity ratio of the narrow-band lights based on an output from the color component ratio measurement section and performs color correction to cause the illumination light to be a desired color;
an optical combiner which combines the narrow-band lights into the illumination light;
an illumination light guide which guides the illumination light obtained by combining; and
a measurement light branch which branches part of the illumination light from the illumination light guide as a measurement light to measure the color component ratio, and guides the measurement light to the color component ratio measurement section, not via the observation object;
wherein the light quantity ratio adjustment circuit comprises a storage circuit which stores an appropriate color component ratio obtained when the illumination light has a desired color; and
the light quantity ratio adjustment circuit adjusts the light quantity ratio of the narrow-band lights so that the color component ratio of the illumination light is made equal to the appropriate color component ratio.

20. The endoscope system according to claim 19, wherein:
the illumination section is configured to radiate a plurality of illumination lights having different spectra for different purposes of observation; and
the storage circuit stores the appropriate color component ratio for each of the illumination lights having the different spectra.

21. The endoscope system according to claim 19, comprising an endoscope, and a main body detachably connected to the endoscope, wherein:

the illumination section comprises a light source which emits the illumination light;
the illumination light guide comprises a first light guide and a second light guide;
the measurement light branch guides the illumination light emitted from the first light guide to the second light guide and branches a part of the illumination light to the color component ratio measurement section;
the light source, the optical combiner, the first light guide, the measurement light branch, and the color component ratio measurement section are arranged in the main body; and
the second light guide is arranged in the endoscope.

22. An endoscope system comprising:
an illumination section, including a light source, which sequentially or simultaneously radiates an illumination light being a plurality of narrow-band lights having wavelengths different from each other and having light quantities which are independently controllable, on an observation object;
a color component ratio measurement section which measures a color component ratio of the illumination light;
a light quantity ratio adjustment circuit which adjusts a light quantity ratio of the narrow-band lights based on an output from the color component ratio measurement section and performs color correction to cause the illumination light to be a desired color;
an optical combiner which combines the narrow-band lights into the illumination light;
an illumination light guide which guides the illumination light obtained by combining; and
a measurement light branch which branches part of the illumination light from the illumination light guide as a measurement light to measure the color component ratio, and guides the measurement light to the color component ratio measurement section, not via the observation object;
wherein:
the optical combiner comprises optical fibers;
the illumination light guide comprises a first optical fiber; and
the measurement light branch comprises a second optical fiber, and an optical fiber coupler which branches the illumination light guided in the first optical fiber to the second optical fiber;
the first optical fiber and the second optical fiber are single optical fibers, respectively;
the optical fiber coupler is formed by fusing the first optical fiber and the second optical fiber; and
at an optical path between the second optical fiber and the color component separation section is arranged a condenser lens.

* * * * *